United States Patent [19]

Eggers et al.

[11] Patent Number: 5,697,281

[45] Date of Patent: Dec. 16, 1997

[54] SYSTEM AND METHOD FOR ELECTROSURGICAL CUTTING AND ABLATION

[75] Inventors: Philip E. Eggers, Dublin, Ohio; Hira V. Thapliyal, Los Altos, Calif.

[73] Assignee: Arthrocare Corporation, Sunnyvale, Calif.

[21] Appl. No.: 485,219

[22] Filed: Jun. 7, 1995

Related U.S. Application Data

[63] Continuation-in-part of Ser. No. 446,767, Jun. 2, 1995, which is a continuation-in-part of Ser. No. 59,681, May 10, 1993, abandoned, which is a continuation-in-part of Ser. No. 958,977, Oct. 9, 1991, Pat. No. 5,366,443, which is a continuation-in-part of Ser. No. 817,575, Jan. 7, 1992, abandoned.

[51] Int. Cl.$^6$ ............................................. A61B 1/00
[52] U.S. Cl. .................................... 604/114; 604/22
[58] Field of Search ................... 604/65, 49, 22, 604/113, 114, 41; 606/42, 39, 27–32, 35, 38, 41

[56] References Cited

U.S. PATENT DOCUMENTS

| | | | |
|---|---|---|---|
| 2,050,904 | 8/1936 | Trice . | |
| 4,202,337 | 5/1980 | Hren et al. | 128/303 |
| 4,228,800 | 10/1980 | Degler, Jr. et al. | 128/303 |
| 4,326,529 | 4/1982 | Doss | 128/303.1 |
| 4,381,007 | 4/1983 | Doss | 128/303.1 |
| 4,476,862 | 10/1984 | Pao | 128/303.17 |
| 4,532,924 | 8/1985 | Auth et al. | 128/303 |
| 4,567,890 | 2/1986 | Ohta et al. | 128/303.13 |
| 4,593,691 | 6/1986 | Lindstrom et al. | 128/303 |
| 4,658,817 | 4/1987 | Hardy | 128/303 |
| 4,674,499 | 6/1987 | Pao . | |
| 4,709,698 | 12/1987 | Johnston et al. | 128/303 |
| 4,765,331 | 8/1988 | Petruzzi et al. | 128/303 |
| 4,931,047 | 6/1990 | Broadwin . | |
| 4,936,301 | 6/1990 | Rexroth et al. . | |
| 4,943,290 | 7/1990 | Rexroth et al. . | |
| 4,955,377 | 9/1990 | Lennox et al. | 128/401 |
| 4,967,765 | 11/1990 | Turner et al. | 128/785 |
| 4,976,711 | 12/1990 | Parins et al. | 606/48 |

(List continued on next page.)

FOREIGN PATENT DOCUMENTS

| | | | |
|---|---|---|---|
| 515 867 | 12/1992 | European Pat. Off. | A61B 17/36 |
| 0 740 926 | 11/1996 | European Pat. Off. | A61B 17/39 |
| WO 90/07303 | 7/1990 | WIPO | A61B 17/39 |
| WO 92/21278 | 12/1992 | WIPO | A61B 5/04 |
| WO 93/13816 | 7/1993 | WIPO | A61B 17/36 |
| WO08654 | 4/1994 | WIPO . | |
| WO 94/14383 | 7/1994 | WIPO | A61B 17/36 |

OTHER PUBLICATIONS

P.C. Nardella (1989) SPIE 1068:42–49 Radio Frequency Energy and Impedance Feedback.

Rand et al. (1985) *J. Arthro. Surg.* 1:242–246 Effect of Electrocautery on Fresh Human Articular Cartilage.

*Primary Examiner*—Manuel Mendez
*Attorney, Agent, or Firm*—Townsend and Townsend and Crew LLP

[57] ABSTRACT

An electrosurgical probe (10) comprises a shaft (13) having an electrode array (12) at its distal end and a connector (19) at its proximal end for coupling the electrode array to a high frequency power supply (28). The shaft includes a return electrode (55, 56) recessed from its distal end and enclosed within an insulating jacket (18). The return electrode defines an inner passage (83) electrically connected to both the return electrode and the electrode array for passage of an electrically conducting liquid (50). By applying high frequency voltage to the electrode array and the return electrode, the electrically conducting liquid generates a current flow path between the target site and the return electrode so that target tissue may be cut or ablated. The probe is particularly useful in dry environments, such as the mouth or abdominal cavity, because the electrically conducting liquid provides the necessary return current path between the return electrode and the target site.

104 Claims, 10 Drawing Sheets

U.S. PATENT DOCUMENTS

| | | | |
|---|---|---|---|
| 4,979,948 | 12/1990 | Geddes et al. | 606/33 |
| 4,998,933 | 3/1991 | Eggers et al. | 606/41 |
| 5,009,656 | 4/1991 | Reimels | 606/48 |
| 5,057,105 | 10/1991 | Malone et al. | 606/28 |
| 5,083,565 | 1/1992 | Parins | 128/642 |
| 5,102,410 | 4/1992 | Dressel | 606/15 |
| 5,108,391 | 4/1992 | Flachenecker et al. | 606/38 |
| 5,178,620 | 1/1993 | Eggers et al. | 606/41 |
| 5,195,959 | 3/1993 | Smith . | |
| 5,197,963 | 3/1993 | Parins . | |
| 5,217,455 | 6/1993 | Tan | 606/9 |
| 5,261,410 | 11/1993 | Alfano et al. | 128/664 |
| 5,267,994 | 12/1993 | Gentelia et al. . | |
| 5,273,524 | 12/1993 | Fox et al. . | |
| 5,277,201 | 1/1994 | Stern | 607/98 |
| 5,281,216 | 1/1994 | Klicek . | |
| 5,282,797 | 2/1994 | Chess | 606/9 |
| 5,290,273 | 3/1994 | Tan | 606/9 |
| 5,290,282 | 3/1994 | Casscells | 606/29 |
| 5,300,069 | 4/1994 | Hunsberger et al. . | |
| 5,304,170 | 4/1994 | Green | 606/9 |
| 5,312,395 | 5/1994 | Tan et al. | 606/9 |
| 5,312,400 | 5/1994 | Bales et al. . | |
| 5,314,406 | 5/1994 | Arias et al. . | |
| 5,324,254 | 6/1994 | Phillips . | |
| 5,334,140 | 8/1994 | Phillips . | |
| 5,334,183 | 8/1994 | Wuchinich . | |
| 5,336,217 | 8/1994 | Buys et al. | 606/9 |
| 5,336,220 | 8/1994 | Ryan et al. . | |
| 5,342,357 | 8/1994 | Nardella . | |
| 5,366,443 | 11/1994 | Eggers et al. | 606/114 |
| 5,370,642 | 12/1994 | Keller | 606/9 |
| 5,380,277 | 1/1995 | Phillips . | |
| 5,380,316 | 1/1995 | Aita et al. | 606/7 |
| 5,383,876 | 1/1995 | Nardella . | |
| 5,383,917 | 1/1995 | Desai et al. | 607/702 |
| 5,389,096 | 2/1995 | Aita et al. | 606/15 |
| 5,395,312 | 3/1995 | Desai . | |
| 5,419,767 | 5/1995 | Eggers et al. | 604/114 |
| 5,423,803 | 6/1995 | Tankovich | 606/9 |
| 5,445,634 | 8/1995 | Keller | 606/9 |
| 5,454,809 | 10/1995 | Janssen | 606/41 |
| 5,569,242 | 10/1996 | Lax et al. | 606/42 |

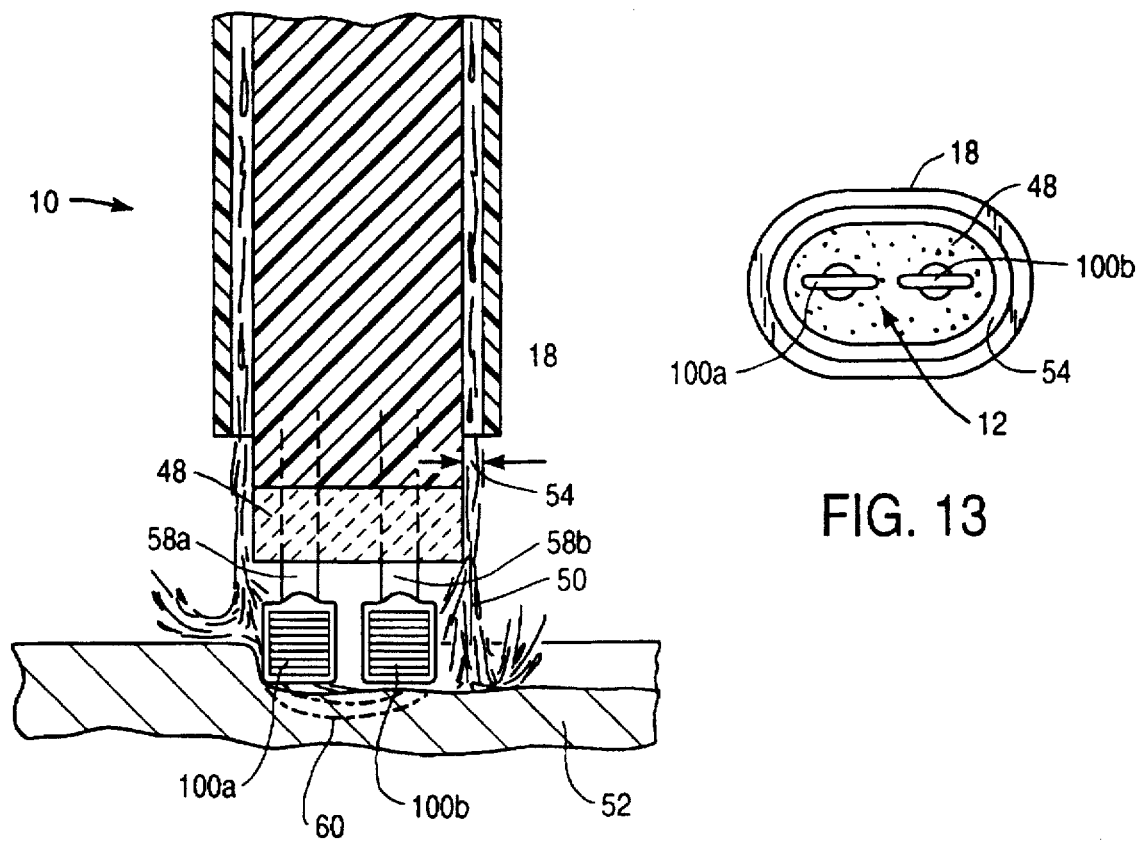
FIG. 13
FIG. 12
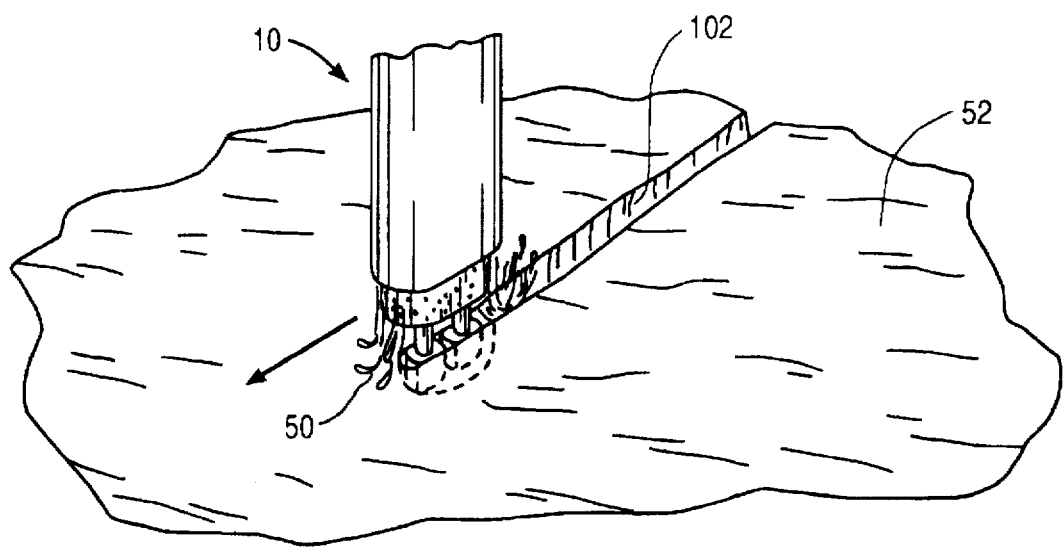
FIG. 14

SYSTEM AND METHOD FOR ELECTROSURGICAL CUTTING AND ABLATION

BACKGROUND OF THE INVENTION

The present invention is a continuation-in-part of application Ser. No. 08/446,767, filed on Jun. 2, 1995, and still pending; which was a continuation-in-part of application Ser. No. 08/059,681, filed on May 10, 1993, now abandoned; which was a continuation-in-part of application Ser. No. 07/958,977, filed on Oct. 9, 1992, now U.S. Pat. No. 5,366,443; which was a continuation-in-part of application Ser. No. 07/817,575, filed on Jan. 7, 1992, now abandoned; the full disclosures of which are incorporated herein by reference.

1. Field of the Invention

The present invention relates generally to the field of electrosurgery and, more particularly, to surgical devices and methods which employ high frequency voltage to cut and ablate tissue.

The field of electrosurgery includes a number of loosely related surgical techniques which have in common the application of electrical energy to modify the structure or integrity of patient tissue. Electrosurgical procedures usually operate through the application of very high frequency currents to cut or ablate tissue structures, where the operation can be monopolar or bipolar. Monopolar techniques rely on external grounding of the patient, where the surgical device defines only a single electrode pole. Bipolar devices comprise both electrodes for the application of current between their surfaces.

Electrosurgical procedures and techniques are particularly advantageous since they generally reduce patient bleeding and trauma associated with cutting operations. Additionally, electrosurgical ablation procedures, where tissue surfaces and volume may be reshaped, cannot be duplicated through other treatment modalities.

Current electrosurgical devices and procedures, however, suffer from a number of disadvantages. For example, monopolar devices generally direct electric current along a defined path from the exposed or active electrode through the patient's body to the return electrode, which is externally attached to a suitable location on the patient. This creates the potential danger that the electric current will flow through undefined paths in the patient's body, thereby increasing the risk of unwanted electrical stimulation to portions of the patient's body. In addition, since the defined path through the patient's body has a relatively high impedance (because of the large distance or resistivity of the patient's body), large voltage differences must typically be applied between the return and active electrodes in order to generate a current suitable for ablation or cutting of the target tissue. This current, however, may inadvertently flow along body paths having less impedance than the defined electrical path, which will substantially increase the current flowing through these paths, possibly causing damage to or destroying surrounding tissue.

Bipolar electrosurgical devices have an inherent advantage over monopolar devices because the return current path does not flow through the patient. In bipolar electrosurgical devices, both the active and return electrode are typically exposed so that they may both contact tissue, thereby providing a return current path from the active to the return electrode through the tissue. One drawback with this configuration, however, is that the return electrode may cause tissue desiccation or destruction at its contact point with the patient's tissue. In addition, the active and return electrodes are typically positioned close together to ensure that the return current flows directly from the active to the return electrode. The close proximity of these electrodes generates the danger that the current will short across the electrodes, possibly impairing the electrical control system and/or damaging or destroying surrounding tissue.

The use of electrosurgical procedures (both monopolar and bipolar) in electrically conductive environments can be further problematic. For example, many arthroscopic procedures require flushing of the region to be treated with isotonic saline (also referred to as normal saline), both to maintain an isotonic environment and to keep the field of viewing clear. The presence of saline, which is a highly conductive electrolyte, can also cause shorting of the electrosurgical electrode in both monopolar and bipolar modes. Such shorting causes unnecessary heating in the treatment environment and can further cause non-specific tissue destruction.

In response to the various problems associated with electrosurgical procedures in electrically conductive environments, new methods and devices have been developed by the applicant. These methods and devices provide selective power delivery to the target tissue while minimizing power delivery to the surrounding electrically conductive irrigant. These methods are particularly useful in isotonic saline filled body cavities, such as arthroscopic, urologic or gynecologic cavities. The irrigant flooded body cavity provides good visibility, facilitates the removal of bubbles or other debris, minimizes the possibility of air embolism and protects certain tissue from dehydration. Such methods and devices are more fully described in previously filed, commonly assigned applications Ser. Nos. 08/059,681, 07/958,977 and 07/817,575, the full disclosures of which have been incorporated by reference.

Many surgical procedures, such as oral, laparoscopic and open surgical procedures, are not performed with the target tissue submerged under an irrigant. In laparoscopic procedures, such as the resection of the gall bladder from the liver, for example, the abdominal cavity is pressurized with carbon dioxide (pneumoperitoneum) to provide working space for the instruments and to improve the surgeon's visibility of the surgical site. Other procedures, such as the ablation of muscle or gingiva tissue in the mouth or the ablation and necrosis of diseased tissue, are also typically performed in a "dry" environment or field (i.e., not submerged under an electrically conducting irrigant).

For these and other reasons, improved systems and methods are desired for the electrosurgical ablation and cutting of tissue. These systems and methods should be capable of providing a direct return current path from the active electrode, through the target site, to the return electrode to minimize the dangers of electrical current flowing through undefined paths in the patient's body. The system should also be configured to minimize contact between the return electrode and surrounding tissue and to avoid current shorting between the active and return electrodes. Preferably, the system will be configured to apply high frequency voltage for the cutting and ablation of tissue in relatively dry environments, such as those encountered in oral, laparoscopic and open surgical procedures.

2. Description of the Background Art

Devices incorporating radio frequency electrodes for use in electrosurgical and electrocautery techniques are described in Rand et al. (1985) J. Arthro. Surg. 1: 242–246 and U.S. Pat. Nos. 5,281,216; 4,943,290; 4,936,301; 4,593, 691; 4,228,800; and 4,202,337. U.S. Pat. Nos. 4,943,290 and 4,036,301 describe methods for injecting non-conducting liquid over the tip of a monopolar electrosurgical electrode to electrically isolate the electrode, while energized, from a surrounding electrically conducting irrigant. U.S. Pat. Nos. 5,195,959 and 4,674,499 describe monopolar and bipolar electrosurgical devices, respectively, that include a conduit for irrigating the surgical site.

SUMMARY OF THE INVENTION

The present invention provides an apparatus and method for selectively applying electrical energy to structures within a patient's body. The apparatus and method allow the surgical team to perform electrosurgical interventions, such as ablation and cutting of body structures, without requiring the tissue to be submerged in an electrically conducting irrigant, such as isotonic saline. The apparatus and method of the present invention are particularly useful for treating and shaping gingiva, for tissue dissection, e.g. separation of gall bladder from the liver, and ablation and necrosis of diseased tissue, such as tumors.

The method of the present invention comprises positioning an electrosurgical probe adjacent the target tissue so that at least one active electrode is brought into at least partial contact or close proximity with the target site. Electrically conducting liquid, such as isotonic saline, is directed through a fluid path past a return electrode and to the target site to generate a current flow path between the target site and the return electrode. High frequency voltage is then applied between the active and return electrode through the current flow path created by the electrically conducting liquid in either a bipolar or monopolar manner. The probe may then be translated, reciprocated or otherwise manipulated to cut the tissue or effect the desired depth of ablation.

The above described method is particularly effective in a dry environment (i.e., the tissue is not submerged in fluid), such as open, laparoscopic or oral surgery, because the electrically conducting liquid provides a suitable current flow path from the target site to the return electrode. The active electrode is preferably disposed at the distal end of the probe and the return electrode is spaced from the active electrode and enclosed within an insulating sheath. This minimizes exposure of the return electrode to surrounding tissue and minimizes possible shorting of the current between the active and return electrodes. In oral procedures, the probe may be introduced directly into the cavity of the open mouth so that the active electrode is positioned against gingival or mucosal tissue. In laparoscopic procedures, the probe will typically be passed through a conventional trocar cannula while viewing of the operative site is provided through the use of a laparoscope disposed in a separate cannula.

The apparatus according to the present invention comprises an electrosurgical probe having a shaft with a proximal end, a distal end, and at least one active electrode at or near the distal end. A connector is provided at or near the proximal end of the shaft for electrically coupling the active electrode to a high frequency voltage source. A return electrode coupled to the voltage source is spaced a sufficient distance from the active electrode to substantially avoid or minimize current shorting therebetween and to shield the return electrode from tissue. The return electrode may be provided integral with the shaft of the probe or it may be separate from the shaft (e.g., on a liquid supply instrument). In both cases, the return electrode defines an inner passage for flow of electrically conducting liquid therethrough. The liquid is directed through the return electrode and over the active electrode to thereby provide a return current flow path between the tissue target site and the return electrode.

In a preferred aspect of the invention, the active electrode comprises an electrode array having a plurality of electrically isolated electrode terminals disposed over a contact surface, which may be a planar or non-planar surface and which may be located at the distal tip or over a lateral surface of the shaft, or over both the tip and lateral surface(s). The electrode array will include at least two and preferably more electrode terminals, and may further comprise a temperature sensor. In a preferred aspect, each electrode terminal will be connected to the proximal connector by an electrically isolated conductor disposed within the shaft. The conductors permit independent electrical coupling of the electrode terminals to a high frequency power supply and control system with optional temperature monitor for operation of the probe. The control system preferably incorporate active and/or passive current limiting structures, which are designed to limit current flow when the associated electrode terminal is in contact with a low resistance return path back to the return electrode.

The use of such electrode arrays in electrosurgical procedures is particularly advantageous as it has been found to limit the depth of tissue necrosis without substantially reducing power delivery and ablation rates. The voltage applied to each electrode terminal causes electrical energy to be imparted to any body structure which is contacted by, or comes into close proximity with, the electrode terminal, where a current flow through all low electrical impedance paths is preferably but not necessarily limited. It will be appreciated that such low impedance paths generally occur when an electrode terminal does not contact or come into close proximity with the body structure, but rather is in contact with a low impedance environment, such as the saline, or other electrolyte being introduced past the return electrode. The presence of an electrolyte provides a relatively low impedance path back to the common or return electrode.

The apparatus and method of the present invention provide a number of advantages, particularly in respect to the ablation or cutting of tissue. The ability to control current flow through individual electrode terminals minimizes power dissipation into the surrounding medium. Limited power dissipation, in turn, permits the use of electrolytic irrigants, such as isotonic saline, to create a current flow path between the active electrode terminals and the return electrode. The isotonic saline may also be used to simultaneously irrigate the surgical site, which provides a number of well known physiological advantages. In addition, the ability to operate in a bipolar or quasi-bipolar mode reduces the risk of unwanted electrical stimulation from return current flowing through the patient's body, which can cause muscle spasms and can limit the depth of tissue necrosis during ablative resection.

A further understanding of the nature and advantages of the invention will become apparent by reference to the remaining portions of the specification and drawings.

BRIEF DESCRIPTION OF THE DRAWINGS

FIG. 12 is a schematic view of an electrosurgical probe having two screwdriver-shaped electrodes extending from the distal end;

FIG. 13 is an end view of the probe of FIG. 12; and

FIG. 14 illustrates use of the probe of FIG. 12 for the rapid cutting of tissue.

DESCRIPTION OF THE PREFERRED EMBODIMENTS

Figure 1:
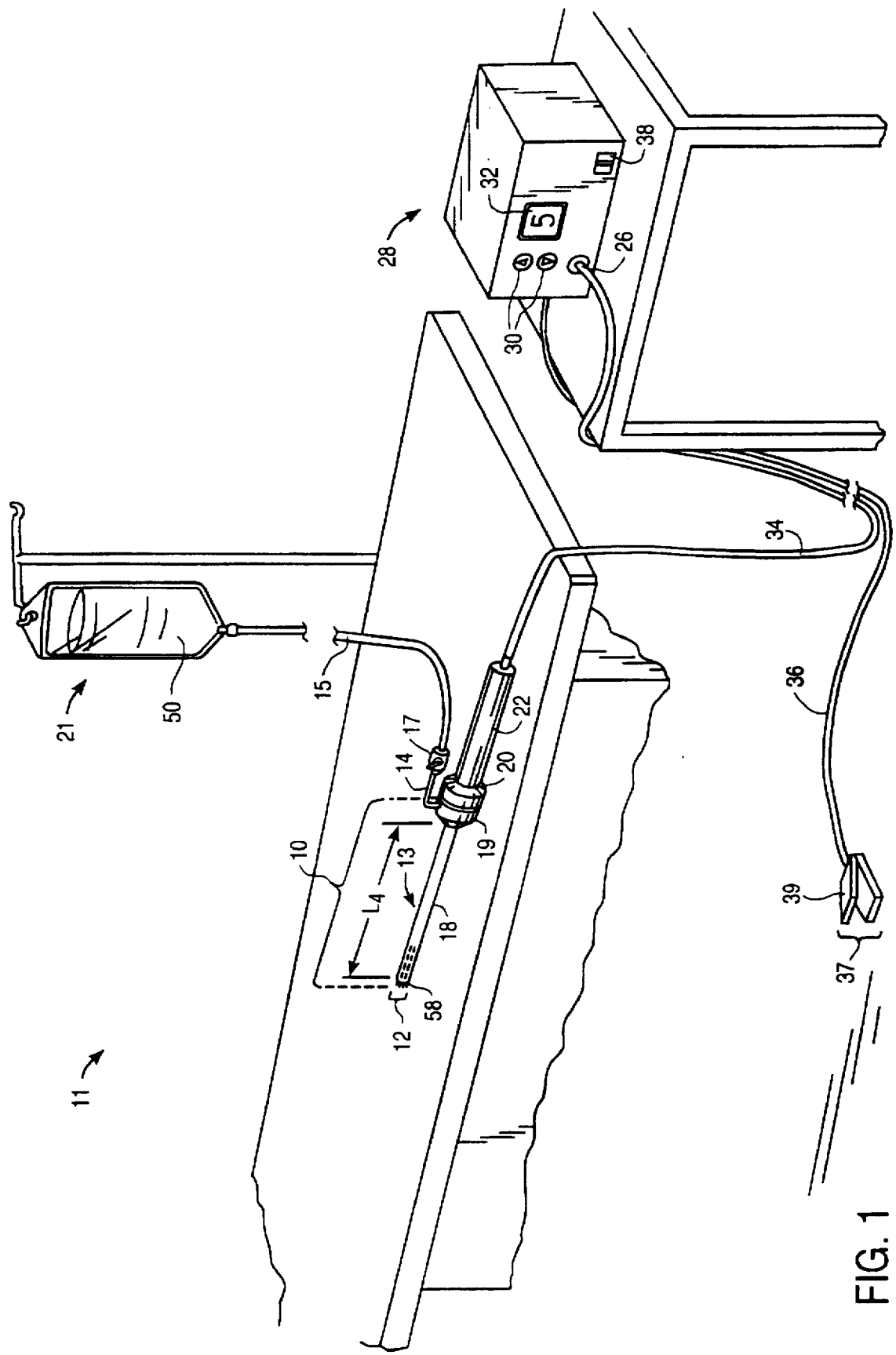
FIG. 1 is a perspective view of the electrosurgical system including an electrosurgical probe, an electrically conducting liquid supply and an electrosurgical power supply constructed in accordance with the principles of the present invention.

The present invention provides an apparatus and method for selectively applying electrical energy to a target location within a patient's body, such as solid tissue or the like, particularly including gingival tissues and mucosal tissues located in the mouth. In addition, tissues which may be treated by the system and method of the present invention include tumors, abnormal tissues, and the like. For convenience, the remaining disclosure will be directed specifically to the cutting, shaping or ablation of gingival or mucosal tissue in oral surgical procedures, but it will be appreciated that the system and method can be applied equally well to procedures involving other tissues of the body, as well as to other procedures including open surgery, laparoscopic surgery, thoracoscopic surgery, and other endoscopic surgical procedures.

The present invention uses an electrode array including a plurality of independently current-limited and/or power-controlled electrode terminals distributed over a distal contact surface of a probe to apply electrical energy selectively to the target tissue while limiting the unwanted application of electrical energy to the surrounding tissue and environment resulting from power dissipation into surrounding electrically conductive liquids, such as blood, normal saline, and the like.

The electrosurgical probe will comprise a shaft having a proximal end and a distal end which supports an electrode array near its distal end. The shaft may assume a wide variety of configurations, with the primary purpose being to mechanically support the electrode array and permit the treating physician to manipulate the array from a proximal end of the shaft. Usually, the shaft will be a narrow-diameter rod or tube, more usually having dimensions which permit it to be introduced into a body cavity, such as the mouth or the abdominal cavity, through an associated trocar or cannula in a minimally invasive procedure, such as arthroscopic, laparoscopic, thoracoscopic, and other endoscopic procedures. Thus, the shaft will typically have a length of at least 5 cm for oral procedures and at least 10 cm, more typically being 20 cm, or longer for endoscopic procedures. The shaft will typically have a diameter of at least 1 mm and frequently in the range from 1 to 10 mm. The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode array. The shaft will usually include a plurality of wires or other conductive elements running axially therethrough to permit connection of the electrode array to a connector at the proximal end of the shaft. Specific shaft designs will be described in detail in connection with the figures hereinafter.

The circumscribed area of the electrode array is in the range from 0.25 mm$^2$ to 75 mm$^2$, preferably from 0.5 mm$^2$ to 40 mm$^2$, and will usually include at least two isolated electrode terminals, more usually at least four electrode terminals, preferably at least six electrode terminals, and often 50 or more electrode terminals, disposed over the distal contact surfaces on the shaft. By bringing the electrode array(s) on the contact surface(s) against or in close proximity with the target tissue and applying high frequency voltage between the array(s) and an additional common or return electrode in direct or indirect contact with the patient's body, the target tissue is selectively ablated or cut, permitting selective removal of portions of the target tissue while desirably minimizing the depth of necrosis to surrounding tissue. In particular, this invention provides a method and apparatus for effectively ablating and cutting tissue which may be located in close proximity to other critical organs, vessels or structures (e.g., teeth, bone) by simultaneously (1) causing electrically conducting liquid to flow between the common and active electrodes, (2) applying electrical energy to the target tissue surrounding and immediately adjacent to the tip of the probe, (3) bringing the active electrode(s) in contact or close proximity with the target tissue using the probe itself, and (4) optionally moving the electrode array axially and/or transversely over the tissue.

Each individual electrode terminal in the electrode array is electrically insulated from all other electrode terminals in the array within said probe and is connected to a power source which is isolated from each of the other electrodes in the array or to circuitry which limits or interrupts current flow to the electrode when low resistivity material (e.g., blood or electrically conductive saline irrigant) causes a lower impedance path between the common electrode and the individual electrode terminal. The isolated power sources for each individual electrode may be separate power supply circuits having internal impedance characteristics which limit power to the associated electrode terminal when a low impedance return path is encountered, may be a single power source which is connected to each of the electrodes through independently actuatable switches or may be provided by independent current limiting elements, such as inductors, capacitors, resistors and/or combinations thereof.

The tip region of the probe is thus composed of many independent electrode terminals designed to deliver electrical energy in the vicinity of the tip. The selective application of electrical energy to of the target tissue is achieved by connecting each individual electrode terminal and the common electrode to a power source having independently controlled or current limited channels. The common electrode may be a tubular member of conductive material proximal to the electrode array at the tip which also serves as a conduit for the supply of the electrically conducting liquid between the active and common electrodes. The application of high frequency voltage between the common electrode and the electrode array results in the generation of high electric field intensities at the distal tips of the electrodes with conduction of high frequency current from each individual electrode terminal to the said common electrode. The current flow from each individual electrode terminal to the common electrode is controlled by either active or passive means, or a combination thereof, to deliver electrical energy to the target tissue while minimizing energy delivery to surrounding (non-target) tissue and any conductive fluids which may be present (e.g., blood, electrolytic irrigants such as saline, and the like).

In a preferred aspect, this invention takes advantage of the differences in electrical resistivity between the target tissue (e.g., gingiva, muscle, fascia, tumor or other connective tissue) and the surrounding conductive liquid (e.g., isotonic saline irrigant). By way of example, for any selected level of applied voltage, if the electrical conduction path between the common electrode and one of the individual electrode terminals within the electrode array is isotonic saline irrigant liquid (having a relatively low electrical impedance), the current control means connected to the individual electrode will limit current flow so that the heating of intervening conductive liquid is minimized. On the other hand, if a portion of or all of the electrical conduction path between the common electrode and one of the individual electrode terminals within the electrode array is gingival tissue (having a relatively higher electrical impedance), the current control circuitry or switch connected to the individual electrode will allow current flow sufficient for the deposition of electrical energy and associated ablation or electrical breakdown of the target tissue in the immediate vicinity of the electrode surface.

The application of a high frequency voltage between the common or return electrode and the electrode array for appropriate time intervals effects ablation, cutting or reshaping of the target tissue. The tissue volume over which energy is dissipated (i.e., a high voltage gradient exists) may be precisely controlled, for example, by the use of a multiplicity of small electrodes whose effective diameters range from about 2 mm to 0.01 mm, preferably from about 1 mm to 0.05 mm, and more preferably from about 0.5 mm to 0.1 mm. Electrode areas for both circular and non-circular terminals will have a contact area (per electrode) below 5 mm$^2$, preferably being in the range from 0.0001 mm$^2$ to 1 mm$^2$, and more preferably from 0.005 mm$^2$ to 0.5 mm$^2$. The use of small diameter electrode terminals increases the electric field intensity and reduces the extent or depth of tissue necrosis as a consequence of the divergence of current flux lines which emanate from the exposed surface of each electrode terminal. Energy deposition in tissue sufficient for irreversible damage (i.e., necrosis) has been found to be limited to a distance of about one-half to one electrode diameter. This is a particular advantage over prior electrosurgical probes employing single and/or larger electrodes where the depth of tissue necrosis may not be sufficiently limited.

In previous electrosurgical devices, increased power application and ablation rates have been achieved by increasing the electrode area. Surprisingly, with the present invention, it has been found that the total electrode area can be increased (to increase power delivery and ablation rate) without increasing the depth of necrosis by providing multiple small electrode terminals. Preferably, the terminals will be spaced-apart by a distance in the range from about one-half diameter to one diameter for optimum power delivery, as discussed below. The depth of necrosis may be further controlled by switching the applied voltage off and on to produce pulses of current, the pulses being of sufficient duration and associated energy density to effect ablation and/or cutting while being turned off for periods sufficiently long to allow for thermal relaxation between energy pulses. In this manner, the energy pulse duration and magnitude and the time interval between energy pulses are selected to achieve efficient rates of tissue ablation or cutting while allowing the temperature of the treated zone of tissue to "relax" or return to normal physiologic temperatures (usually to within 10° C. of normal body temperature [37° C.], preferably to within 5° C.) before the onset of the next energy (current) pulse.

The rate of energy delivery to the target tissue is controlled by the applied voltage level and duty cycle of the voltage pulse. The use of high frequency current minimizes induced stimulation of muscle tissue or nerve tissue in the vicinity of the body structure being treated. In addition, high frequencies minimize the risk of interfering with the natural pacing of the heart in circumstances where the probe of the present invention is used near the heart.

The power applied to the common electrode and the electrode array will be at high or radio frequency, typically between about 20 kHz and 20 MHz, usually being between about 30 kHz and 2 MHz, and preferably being between about 50 kHz and 400 kHz. The RMS (root mean square) voltage applied will usually be in the range from about 5 volts to 1000 volts, preferably being in the range from about 50 volts to 800 volts, and more preferably being in the range from about 10 volts to 500 volts. Usually, the current level will be selectively limited or controlled and the voltage applied will be independently adjustable, frequently in response to the resistance of tissues and/or fluids in the pathway between an individual electrode and the common electrode. Also, the applied current level may be in response to a temperature control means which maintains the target tissue temperature with desired limits at the interface between the electrode arrays and the target tissue. The desired surface temperature along a propagating surface just beyond the region of ablation will usually be in the range from about 40° C. to 100° C., and more usually from about 50° C. to 60° C. The tissue being ablated immediately adjacent the electrode array may reach even higher temperatures.

The preferred power source of the present invention delivers a high frequency current selectable to generate average power levels ranging from tens of milliwatts to tens of watts per electrode, depending on the target tissue being ablated, the rate of ablation desired or the maximum allowed temperature selected for the probe tip. The power source allows the user to select the current level according to the specific requirements of a particular oral surgery, open surgery or other endoscopic surgery procedure.

The power source will be current limited or otherwise controlled so that undesired heating of electrically conductive fluids or other low electrical resistance media does not occur. In a presently preferred embodiment of the present invention, current limiting inductors are placed in series with each independent electrode terminal, where the inductance of the inductor is in the range of 20 uH to 5000 uH, depending on the electrical properties of the target tissue, the desired ablation rate and the operating frequency. Alternatively, capacitor-inductor (LC) circuit structures may be employed, as described previously in co-pending PCT application No. PCT/US94/05168, which has already been incorporated herein by reference. Additionally, current limiting resistors may be selected having a large positive temperature coefficient of resistance so that, as the current level begins to rise for any individual electrode in contact with a low resistance medium (e.g., saline irrigant), the resistance of the current limiting resistor increases significantly, thereby minimizing the power delivery from said electrode into the low resistance medium (e.g., saline irrigant).

As an alternative to such passive circuit structures, regulated current flow to each electrode terminal may be provided by a multi-channel power supply. A substantially constant current level for each individual electrode terminal within a range which will limit power delivery through a low resistance path, e.g., isotonic saline irrigant, would be selected by the user to achieve the desired rate of cutting or ablation. Such a multi-channel power supply thus provides a substantially constant current source with selectable current level in series with each electrode terminal, wherein all electrodes will operate at or below the same, user selectable maximum current level. Current flow to all electrode terminals could be periodically sensed and stopped if the temperature measured at the surface of the electrode array exceeds user selected limits. Particular control system designs for implementing this strategy are well within the skill of the art.

Yet another alternative involves the use of one or several power supplies which allow one or several electrodes to be simultaneously energized and which include active control means for limiting current levels below a preselected maximum level. In this arrangement, only one or several electrodes would be simultaneously energized for a brief period. Switching means would allow the next one or several electrodes to be energized for a brief period. By sequentially energizing one or several electrodes, the interaction between adjacent electrodes can be minimized (for the case of energizing several electrode positioned at the maximum possible spacing within the overall envelope of the electrode array) or eliminated (for the case of energizing only a single electrode at any one time). As before, a resistance measurement means may be employed for each electrode prior to the application of power wherein a (measured) low resistance (below some preselected level) will prevent that electrode from being energized during given cycle. By way of example, the sequential powering and control scheme of the present invention would function in a manner similar to an automobile distributor. In this example, an electrical contact rotates past terminals connected to each spark plug. In this example, each spark plug corresponds to the exposed surface of each of the electrodes. In addition, the present invention includes the means to measure the resistance of the medium in contact with each electrode and cause voltage to be applied only if the resistance exceeds a preselected level.

The electrode array is formed over a contact surface on the shaft of the electrosurgical probe. The common (return) electrode surface will be recessed relative to the distal end of the probe and may be recessed within the conduit provided for the introduction of electrically conducting liquid to the site of the target tissue and array of active electrodes. In the exemplary embodiment, the shaft will be cylindrical over most of its length, with the contact surface being formed at the distal end of the shaft. In the case of laparoscopic or endoscopic applications, the contact surface may be recessed since it helps protect and shield the electrode terminals on the surface while they are being introduced, particularly while being introduced through the working channel of a trocar channel or a viewing scope.

The area of the contact surface can vary widely, and the contact surface can assume a variety of geometries, with particular areas in geometries being selected for specific applications. Electrode array contact surfaces can have areas in the range from 0.25 $mm^2$ to 50 $mm^2$, usually being from 1 $mm^2$ to 20 $mm^2$. The geometries can be planar, concave, convex, hemispherical, conical, or virtually any other regular or irregular shape. Most commonly, the electrode arrays will be formed at the distal tip of the electrosurgical probe shaft, frequently being planar, disk-shaped, or hemispherical surfaces for use in reshaping procedures or being linear arrays for use in cutting. Alternatively or additionally, the electrode arrays may be formed on lateral surfaces of the electrosurgical probe shaft (e.g., in the manner of a spatula), facilitating access to certain body structures in electrosurgical procedures.

Referring to the drawings in detail, wherein like numerals indicate like elements, an electrosurgical system 11 is shown constructed according to the principles of the present invention. Electrosurgical system 11 generally comprises an electrosurgical probe 10 connected to a power supply 28 for providing high frequency voltage to a target tissue 52 and a liquid source 21 for supplying electrically conducting fluid 50 to probe 10.

In an exemplary embodiment as shown in FIG. 1, electrosurgical probe 10 includes an elongated shaft 13 which may be flexible or rigid, with flexible shafts optionally including support cannulas or other structures (not shown). Probe 10 includes a connector 19 at its proximal end and an array 12 of electrode terminals 58 disposed on the distal tip of shaft 13. A connecting cable 34 has a handle 22 with a connector 20 which can be removably connected to connector 19 of probe 10. The proximal portion of cable 34 has a connector 26 to couple probe 10 to power supply 28. The electrode terminals 58 are electrically isolated from each other and each of the terminals 58 is connected to an active or passive control network within power supply 28 by means of a plurality of individually insulated conductors 42 (see FIG. 2C). Power supply 28 has a selection means 30 to change the applied voltage level. Power supply 28 also includes means for energizing the electrodes 58 of probe 10 through the depression of a pedal 39 in a foot pedal 37 positioned close to the user. The foot pedal 37 may also include a second pedal (not shown) for remotely adjusting the energy level applied to electrodes 58. The specific design of a power supply which may be used with the electrosurgical probe of the present invention is described in parent application PCT/US94 05168, the full disclosure of which has previously been incorporated herein by reference.

Figure 2A:
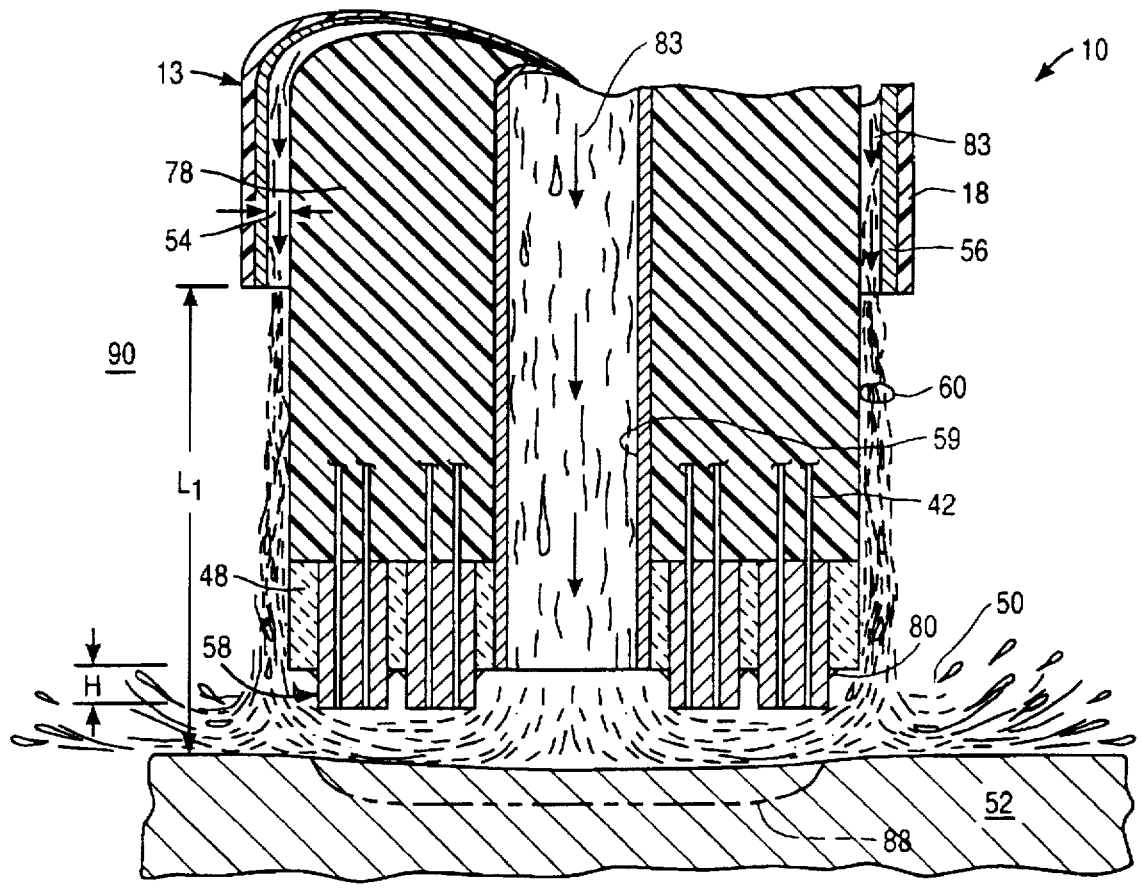
FIG. 2A is an enlarged, cross-sectional view of the distal tip of the electrosurgical probe of FIG. 1 illustrating an electrode arrangement suitable for rapid cutting and ablation of tissue structures.
Figure 2B:
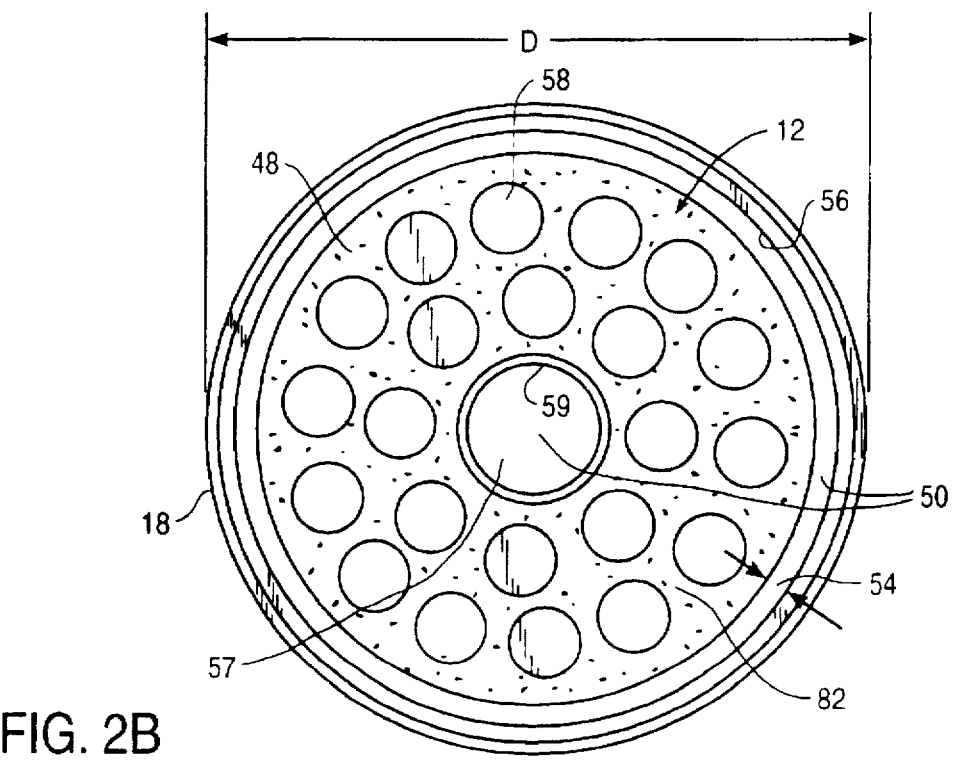
FIG. 2B is an enlarged end view of the distal tip of the electrosurgical probe of FIG. 1.
Figure 5:
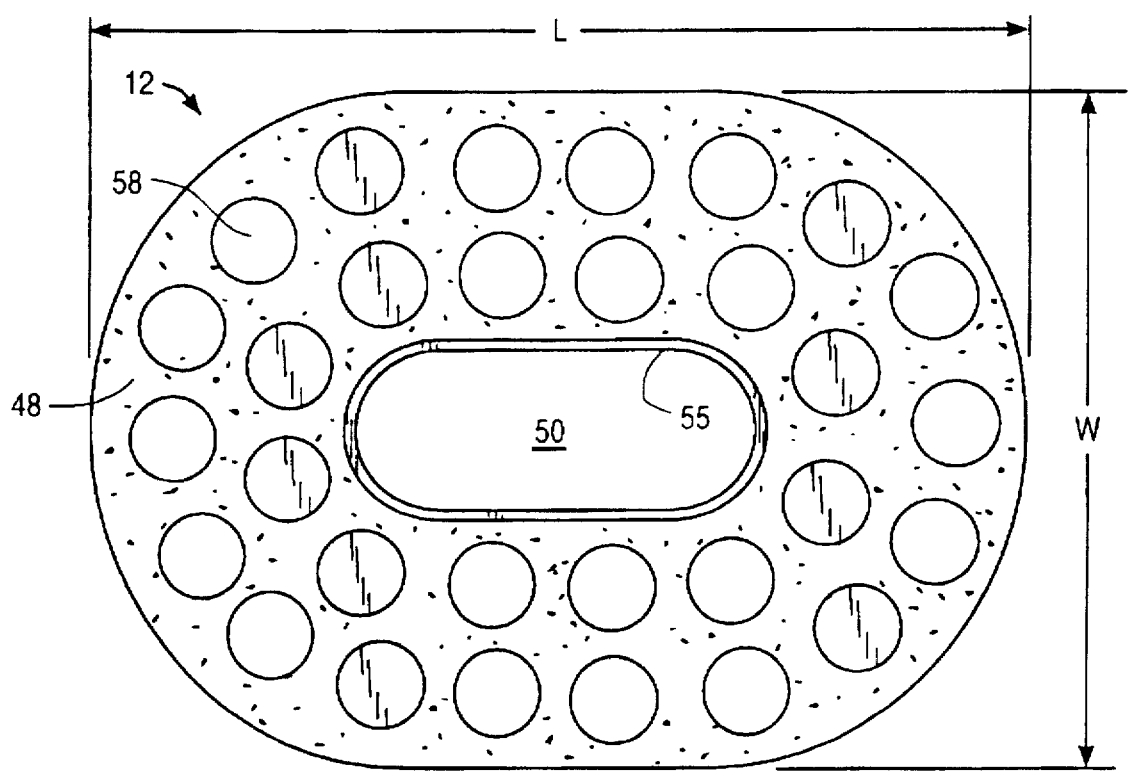
FIG. 5 is an end view of an another embodiment of the electrosurgical probe of FIG. 1.

Referring to FIGS. 2A and 2B, the electrically isolated electrode terminals 58 are spaced-apart over an electrode array surface 82. The electrode array surface 82 and individual electrode terminals 58 will usually have dimensions within the ranges set forth above. In the preferred embodiment, the electrode array surface 82 has a circular cross-sectional shape with a diameter D (FIG. 2B) in the range from 1 mm to 10 mm. Electrode array surface 82 may also have an oval shape, having a length L in the range of 1 mm to 20 mm and a width W in the range from 0.5 mm to 7 mm, as shown in FIG. 5. The individual electrode terminals 58 will protrude over the electrode array surface 82 by a distance (H) from 0 mm to 2 mm, preferably from 0 mm to 1 mm (see FIG. 3). As described above, electrode terminals which are flush with the surface, or protrude by a minimum distance, will provide less aggressive ablation and are particularly suitable for smoothing of treated tissue surfaces and providing hemostasis to inhibit or prevent bleeding of treated surfaces.

The electrode terminals 58 are preferably composed of a refractory, electrically conductive metal or alloy, such as platinum, platinum alloys, titanium, titanium alloys and the like. Platinum is the preferred choice for electrode terminal material since it is biocompatible, has a low erosion rate, and can be readily fabricated and attached to conductors 42 within the shaft 13 of electrosurgical probe 10. As shown in FIG. 2B, the electrode terminals 58 are anchored in a support matrix 48 of suitable insulating material (e.g., ceramic or glass material, such as alumina, zirconia and the like) which could be formed at the time of manufacture in a flat, hemispherical or other shape according to the requirements of a particular procedure. The preferred support matrix material is alumina, available from Kyocera Industrial Ceramics Corporation, Elkgrove, Ill., because of its high thermal conductivity, good electrically insulative properties, high flexural modulus, resistance to carbon tracking, biocompatibility, and high melting point.

Figure 3:
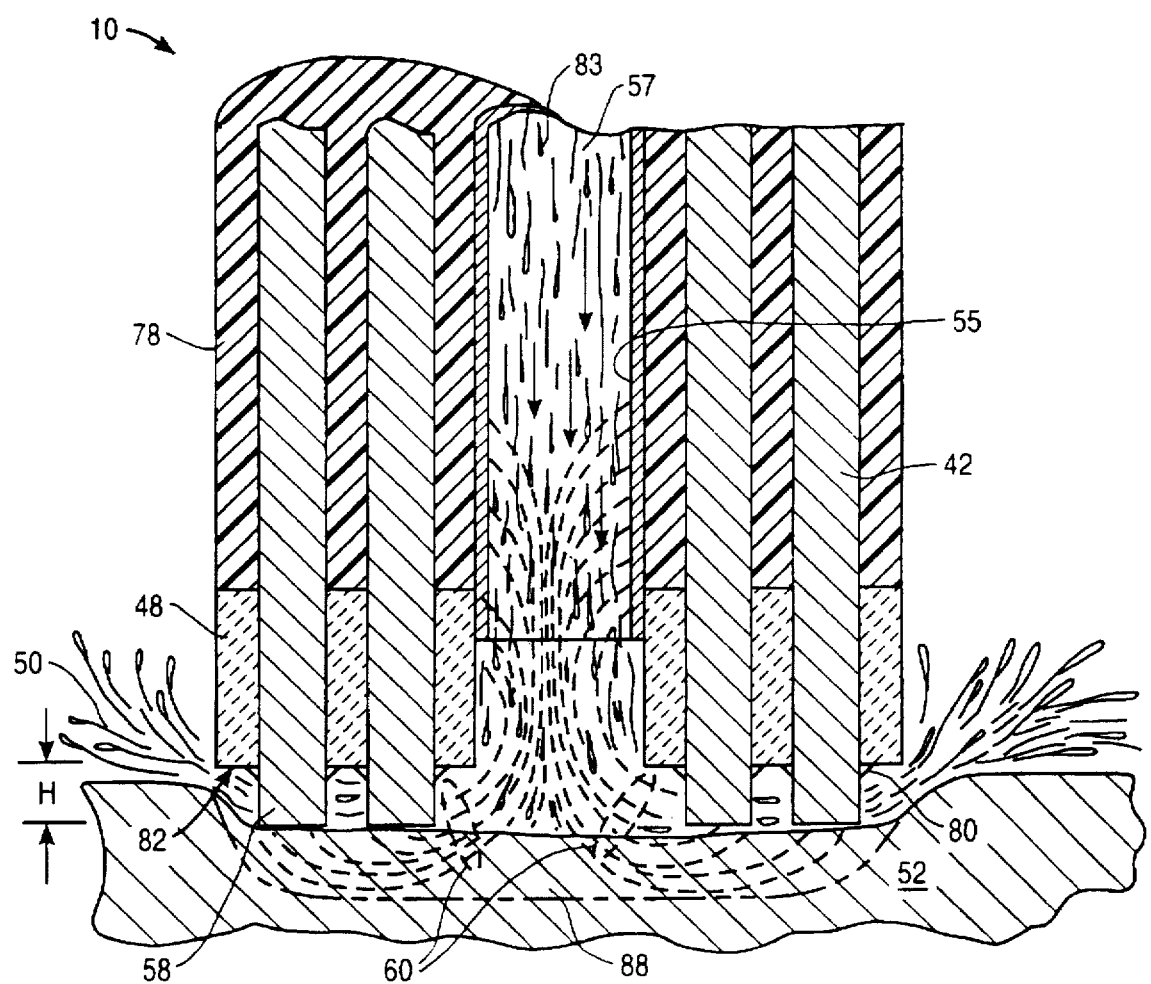
FIG. 3 is a detailed cross-sectional view of an alternative embodiment of the electrosurgical probe of FIG. 1.

As shown in FIG. 2A, the support matrix 48 is adhesively joined to a tubular support member 78 that extends most or all of the distance between matrix 48 and the proximal end of probe 10. Tubular member 78 preferably comprises an electrically insulating material, such as an epoxy or silicone-based material. In a preferred construction technique, electrode terminals 58 extend through pre-formed openings in the support matrix 48 so that they protrude above electrode array surface 82 by the desired distance H (FIG. 3). The electrodes are then bonded to the distal surface 82 of support matrix 48, typically by an inorganic sealing material 80. Sealing material 80 is selected to provide effective electrical insulation, and good adhesion to both the alumina matrix 48 and the platinum or titanium electrode terminals. Sealing material 80 additionally should have a compatible thermal expansion coefficient and a melting point well below that of platinum or titanium and alumina or zirconia, typically being a glass or glass ceramic.

In the embodiment shown in FIGS. 2A and 2B, probe 10 includes a return electrode 56 for completing the current path between electrode terminals 58 and power supply 28. Return electrode 56 is preferably an annular member positioned around the exterior of shaft 13 of probe 10. Return electrode 56 may fully or partially circumscribe tubular support member 78 to form an annular gap 54 therebetween for flow of electrically conducting liquid 50 therethrough, as discussed below. Gap 54 preferably has a width in the range of 0.25 mm to 4 mm. Return electrode 56 extends from the proximal end of probe 10, where it is suitably connected to power supply 28 via connectors 19, 20, to a point slightly proximal of electrode array surface 82, typically about 1 mm to 10 mm.

Return electrode 56 is disposed within an electrically insulative jacket 18, which is typically formed as one or more electrically insulative sheaths or coatings, such as polytetrafluoroethylene, polyamide, and the like. The provision of the electrically insulative jacket 18 over return electrode 56 prevents direct electrical contact between return electrode 56 and any adjacent body structure. Such direct electrical contact between a body structure (e.g., tendon) and an exposed common electrode member 56 could result in unwanted heating and necrosis of the structure at the point of contact causing necrosis.

Return electrode 56 is preferably formed from an electrically conductive material, usually metal, which is selected from the group consisting of stainless steel, platinum or its alloys, titanium or its alloys, molybdenum or its alloys, and nickel or its alloys. The return electrode 56 may be composed of the same metal or alloy which forms the electrode terminals 58 to minimize any potential for corrosion or the generation of electrochemical potentials due to the presence of dissimilar metals contained within an electrically conductive fluid 50, such as isotonic saline (discussed in greater detail below).

As shown in FIG. 2A, return electrode 56 is not directly connected to electrode terminals 58. To complete this current path so that terminals 58 are electrically connected to return electrode 56 via target tissue 52, electrically conducting liquid 50 (e.g., isotonic saline) is caused to flow along liquid paths 83. Liquid paths 83 are formed by annular gap 54 between outer return electrode 56 and tubular support member 78 and an inner lumen 57 within an inner tubular member 59. The electrically conducting liquid 50 flowing through fluid paths 83 provides a pathway for electrical current flow between target tissue 52 and return electrode 56, as illustrated by the current flux lines 60 in FIG. 2A. When a voltage difference is applied between electrode array 12 and return electrode 56, high electric field intensities will be generated at the distal tips of terminals 58 with current flow from array 12 through the target tissue to the return electrode, the high electric field intensities causing ablation of tissue 52 in zone 88.

Figure 2C:
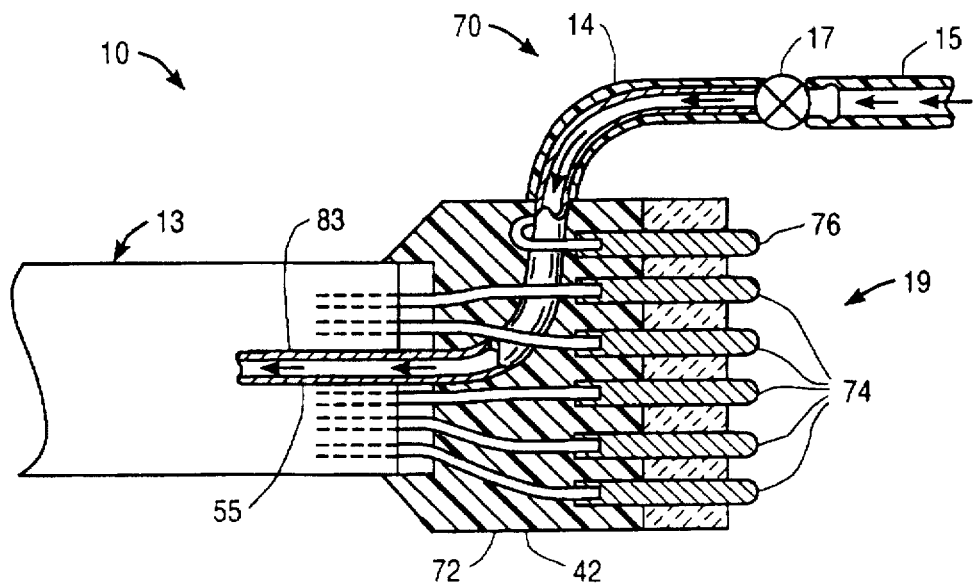
FIG. 2C is a cross-sectional view of the proximal end of the electrosurgical probe, illustrating an arrangement for coupling the probe to the electrically conducting liquid supply of FIG. 1.
Figure 4:
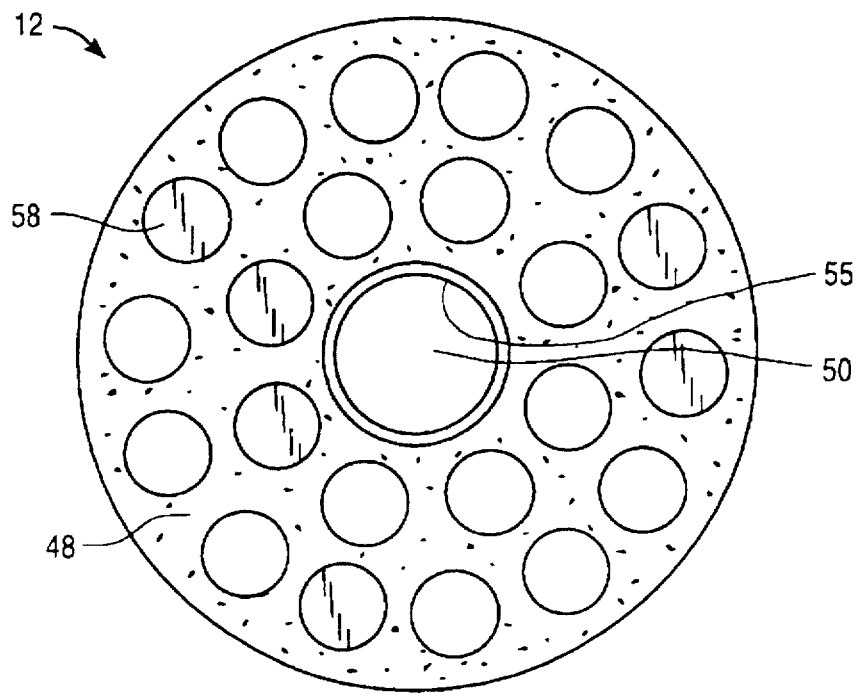
FIG. 4 is an end view of the distal end of the electrosurgical probe of FIG. 3.

FIGS. 2C, 3 and 4 illustrate an alternative embodiment of electrosurgical probe 10 which has a return electrode 55 positioned within tubular member 78. Return electrode 55 is preferably a tubular member defining an inner lumen 57 for allowing electrically conducting liquid 50 (e.g., isotonic saline) to flow therethrough in electrical contact with return electrode 55. In this embodiment, a voltage difference is applied between electrode terminals 58 and return electrode 55 resulting in electrical current flow through the electrically conducting liquid 50 as shown by current flux lines 60 (FIG. 3). As a result of the applied voltage difference and concomitant high electric field intensities at the tips of electrode terminals 58, tissue 52 becomes ablated or transected in zone 88.

FIG. 2C illustrates the proximal or connector end 70 of probe 10 in the embodiment of FIGS. 3 and 4. Connector 19 comprises a plurality of individual connector pins 74 positioned within a housing 72 at the proximal end 70 of probe 10. Electrode terminals 58 and the attached insulating conductors 42 extend proximally to connector pins 74 in connector housing 72. Return electrode 55 extends into housing 72, where it bends radially outward to exit probe 10. As shown in FIGS. 1 and 2C, a liquid supply tube 15 removably couples liquid source 21, (e.g., a bag of fluid elevated above the surgical site or having a pumping device), with return electrode 55. Preferably, an insulating jacket 14 covers the exposed portions of electrode 55. One of the connector pins 76 is electrically connected to return electrode 55 to couple electrode 55 to power supply 28 via cable 34. A manual control valve 17 may also be provided between the proximal end of electrode 55 and supply tube 15 to allow the surgical team to regulate the flow of electrically conducting liquid 50.

Figure 6:
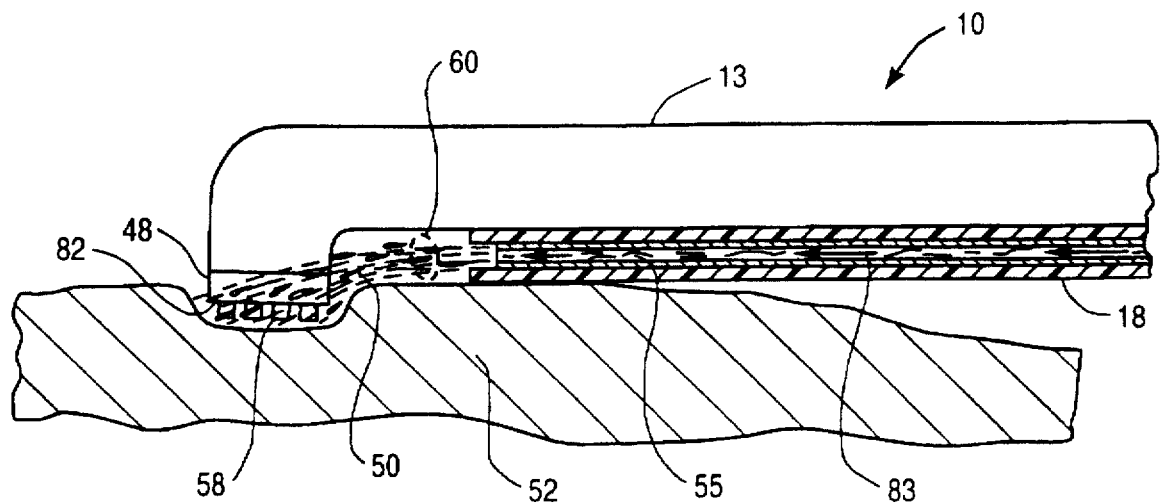
FIG. 6 is a partial cross-sectional side view of a further embodiment of the electrosurgical probe with the electrode array disposed transversely to the axis of the probe.

FIG. 6 illustrates another embodiment of probe 10 where the distal portion of shaft 13 is bent so that electrode terminals extend transversely to the shaft. Preferably, the distal portion of shaft 13 is perpendicular to the rest of the shaft so that electrode array surface 82 is generally parallel to the shaft axis, as shown in FIG. 6. In this embodiment, return electrode 55 is mounted to the outer surface of shaft 13 and is covered with an electrically insulating jacket 18. The electrically conducting fluid 50 flows along flow path 83 through return electrode 55 and exits the distal end of electrode 55 at a point proximal of electrode surface 82. The fluid is directed exterior of shaft to electrode surface 82 to create a return current path from electrode terminals 58, through target tissue 52, to return electrode 55, as shown by current flux lines 60.

Figure 7:
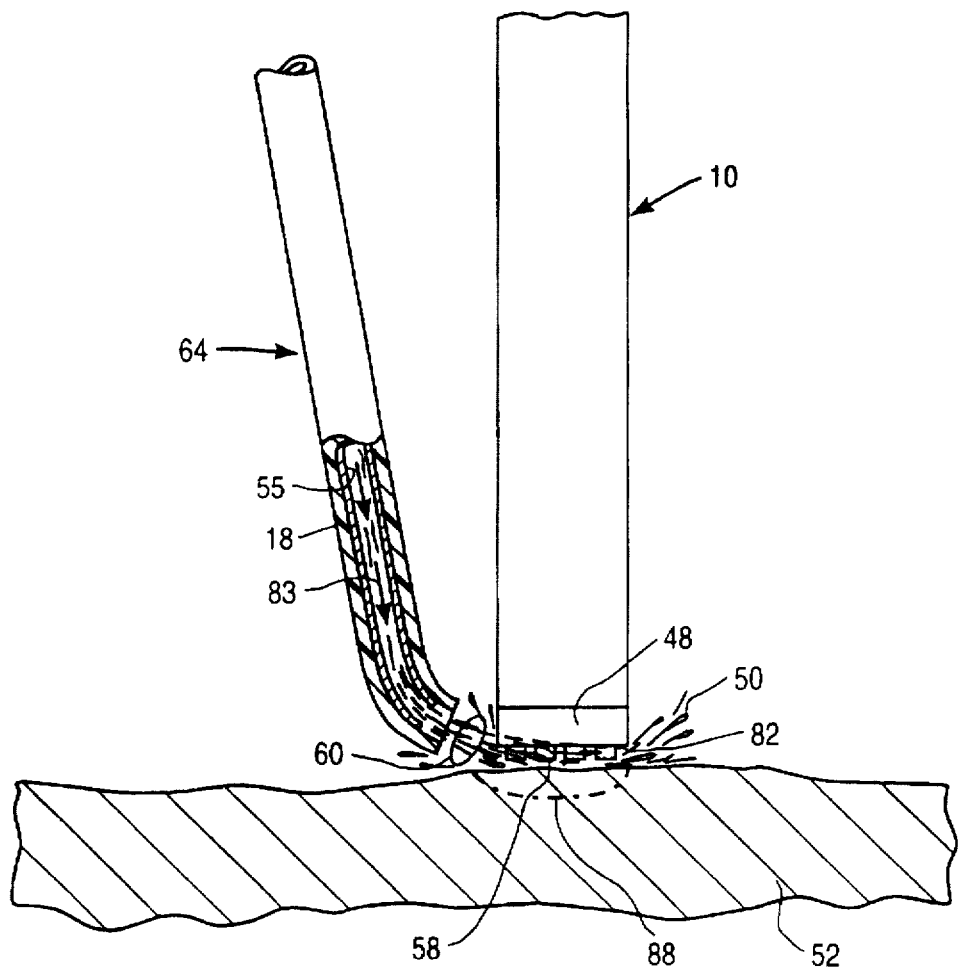
FIG. 7 is a partial front cross-sectional view of an electrosurgical probe and an electrically conductive liquid supply shaft illustrating use of the probe and the shaft in ablating target tissue.

FIG. 7 illustrates another embodiment of the invention where electrosurgical system 11 further includes a liquid supply instrument 64 for supplying electrically conducting fluid 50 between electrode terminals 58 and return electrode 55. Liquid supply instrument 64 comprises an inner tubular member or return electrode 55 surrounded by an electrically insulating jacket 18. Return electrode 55 defines an inner passage 83 for flow of fluid 50. As shown in FIG. 7, the distal portion of instrument 64 is preferably bent so that liquid 50 is discharged at an angle with respect to instrument 64. This allows the surgical team to position liquid supply instrument 64 adjacent electrode surface 82 with the proximal portion of supply instrument 64 oriented at a similar angle to probe 10.

Figure 8:
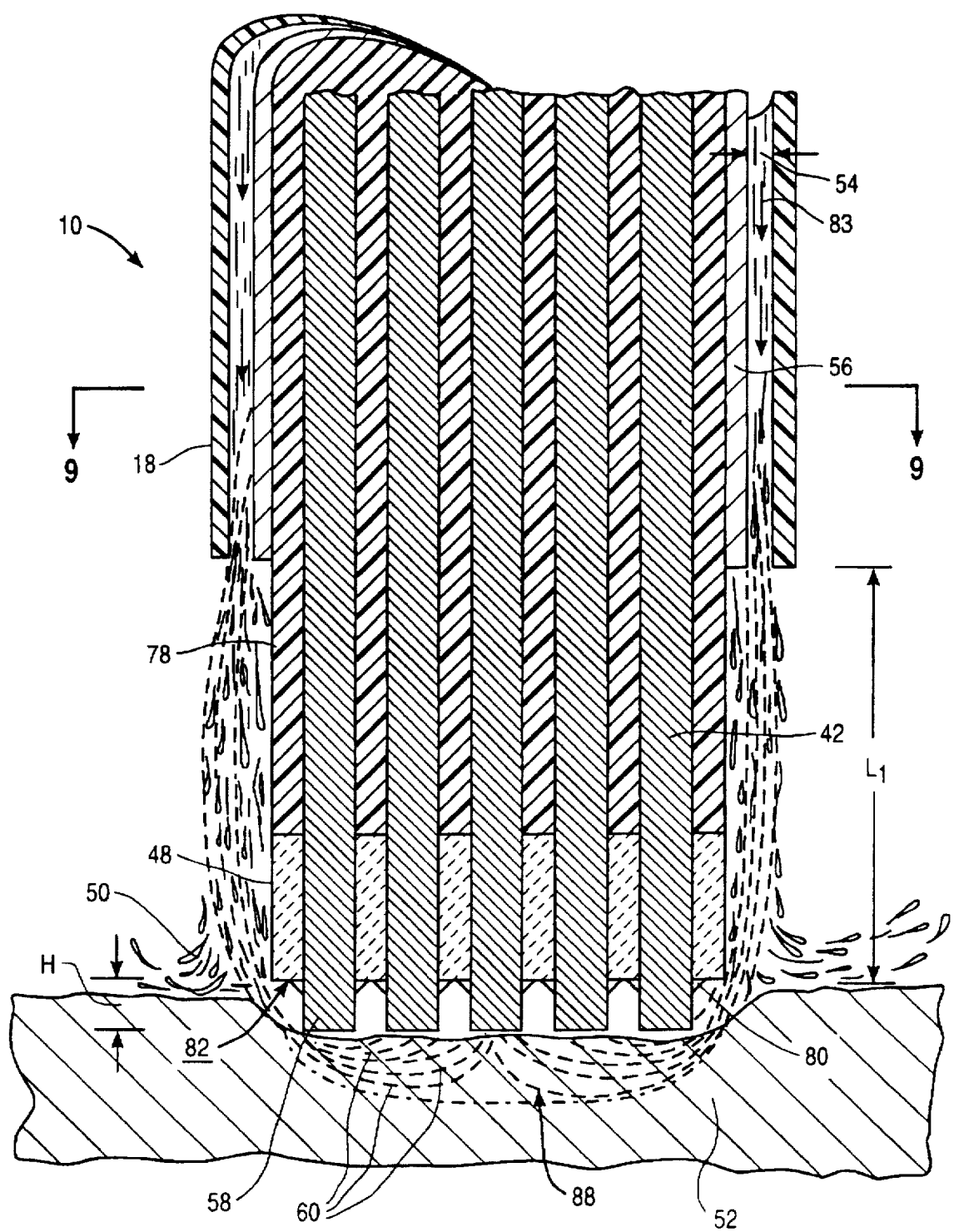
FIG. 8 is an enlarged, cross-sectional view of the distal tip of yet another embodiment of the electrosurgical probe of FIG. 1.
Figure 9:
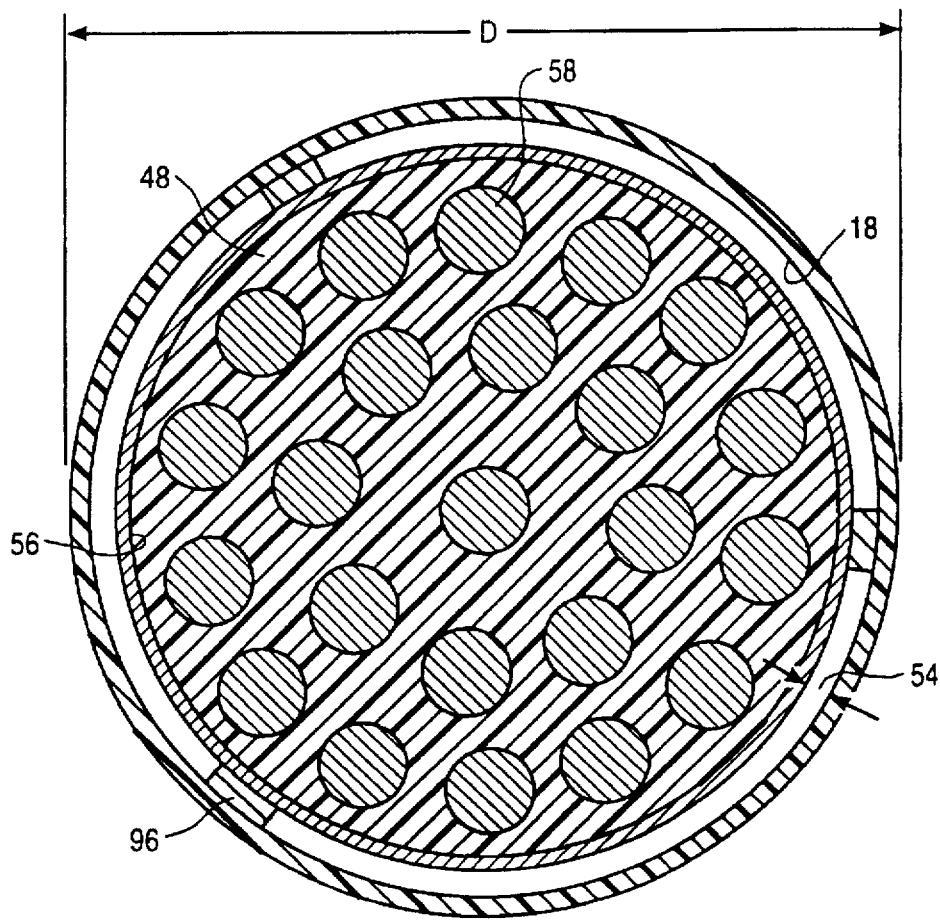
FIG. 9 is a detailed end view of the probe of FIG. 8.

FIGS. 8 and 9 illustrate another embodiment of probe 10 where the return electrode is an outer tubular member 56 that circumscribes support member 78 and conductors 42. Insulating jacket 18 surrounds tubular member 56 and is spaced from member 56 by a plurality of longitudinal ribs 96 to define an annular gap 54 therebetween (FIG. 9). Annular gap preferably has a width in the range of 0.25 mm to 4 mm. Ribs 96 can be formed on either the jacket 18 or member 56. The distal end of return electrode 56 is a distance $L_1$ from electrode surface 82. Distance $L_1$ is preferably about 0.5 to 10 mm and more preferably about 1 to 10 mm.

As shown in FIG. 8, electrically conducting liquid 50 flows through annular gap 54 (in electrical communication with the return electrode) and is discharged through the distal end of gap 54. The liquid 50 is then directed around support member 78 to electrode terminals 58 to provide the current pathway between the electrode terminals and return electrode 56. Since return electrode 56 is proximally recessed with respect to electrode surface 82, contact between the return electrode 56 and surrounding tissue is minimized. In addition, the distance L1 between the active electrode terminals 58 and the return electrode 56 reduces the risk of current shorting therebetween.

The present invention is not limited to an electrode array disposed on a relatively planar surface at the distal tip of probe 10, as described above. Referring to FIGS. 12–14, an alternative probe 10 includes a pair of electrodes 58a, 58b mounted to the distal end of shaft 13. Electrodes 58a, 58b are electrically connected to power supply as described above and preferably have tips 100a, 100b with a screwdriver shape. The screwdriver shape provides a greater amount of "edges" to electrodes 58a, 58b, to increase the electric field intensity and current density at the edges and thereby improve the cutting ability as well as the ability to limit bleeding from the incised tissue (i.e., hemostasis).

As shown in FIG. 12, current flows between electrode tips 100a and 100b as indicated by current flux lines 60 to heat the target tissue 52. The surgical team then moves probe 10 transversely across tissue 52 to effect an incision 102 in tissue 52, as shown in FIG. 14.

Figure 10:
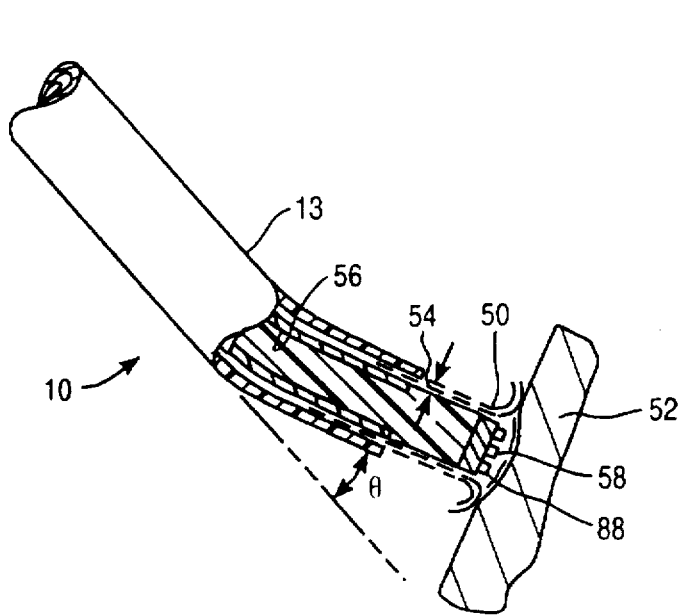
FIG. 10 is a side view of an electrosurgical probe having a shaft with an angled distal portion.
Figure 11:
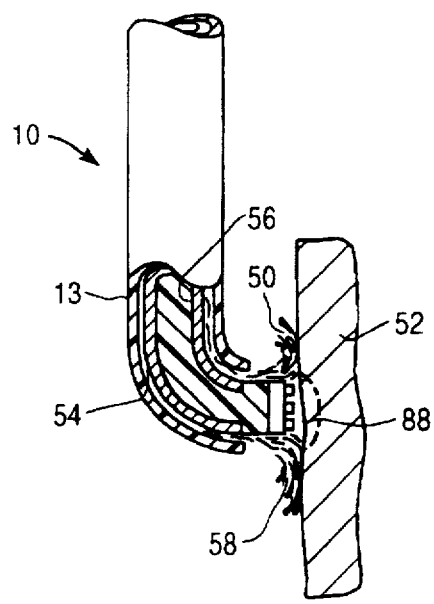
FIG. 11 is a side view of an electrosurgical probe having a shaft with a perpendicular distal portion.

Other modifications and variations can be made to disclose embodiments without departing from the subject invention as defined in the following claims. For example, shaft 13 of probe 10 may have a variety of configurations other than the generally linear shape shown in FIGS. 1–8. For example, shaft 13 may have a distal portion that is angled, in the range of 10° to 30° (FIG. 10) or 90° (FIGS. 11 and 6), to improve access to the operative site of the tissue 52 being ablated or cut (see FIG. 10). A shaft having a 90° bend angle may be particular useful for accessing gingiva located in the back portion of the patient's mouth and a shaft having a 10° to 30° bend angle may be useful for accessing gingiva near or in the front of the patient's mouth.

Figure 15:
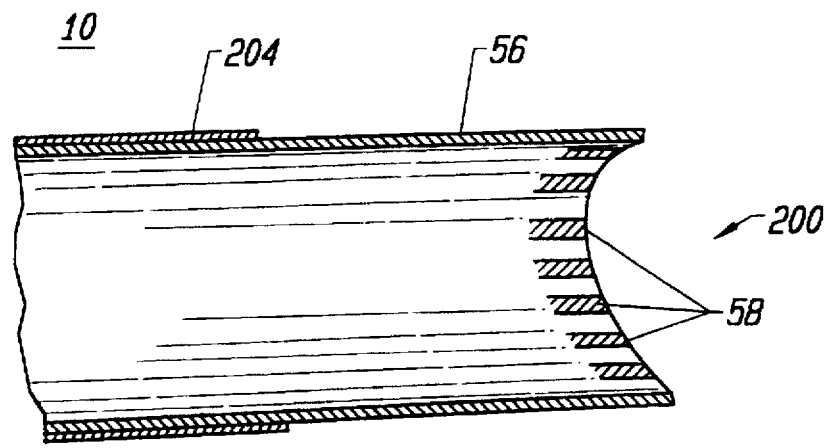
FIG. 15 illustrates another alternative electrode surface configuration for the electrosurgical probe of FIG. 1.

Yet another configuration for tip 200 of probe 10 is shown in FIG. 15 wherein a concave or wedge-shaped arrangement of electrodes 58 is provided to facilitate good contact with target tissue which can be embraced by said concave or wedge-shaped opening. As before, the return electrode 56 may be positioned proximal to probe tip 200.

Figure 16:
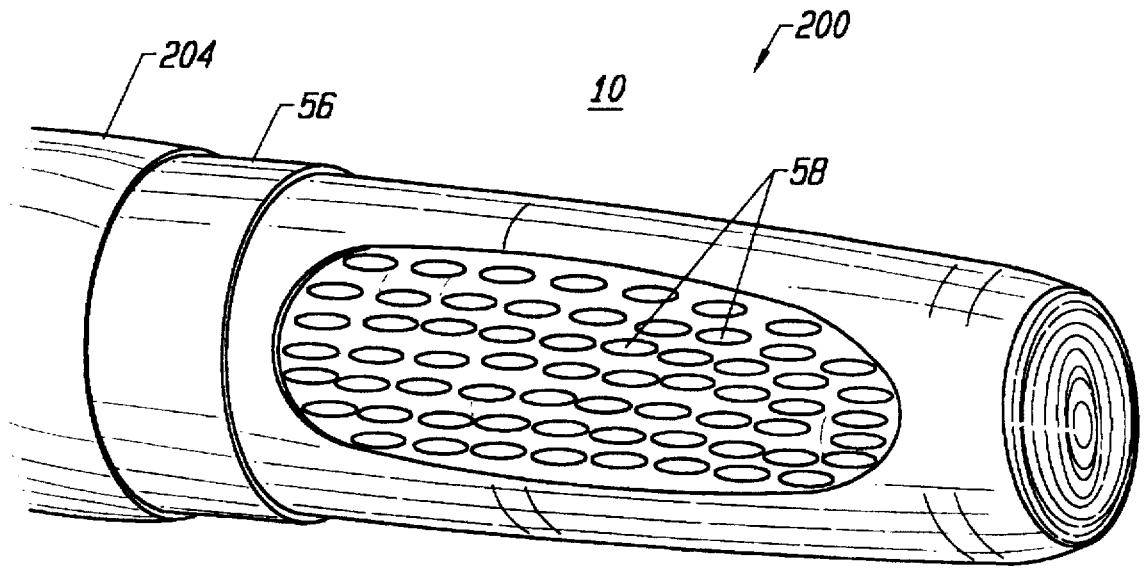
FIG. 16 illustrates a second alternative electrode surface configuration.

Still yet another configuration for tip 200 of probe 10 is shown in FIG. 16 wherein electrodes 58 terminate on the side of the generally tubular (e.g., cylindrical) surface proximal to the distal end of probe 10. This configuration allows the electrode array to be brought into contact with target tissue surfaces which are tangent to the tubular surface of probe 10. As before, return electrode 56 may be positioned proximal to probe tip 200.

Figure 17:
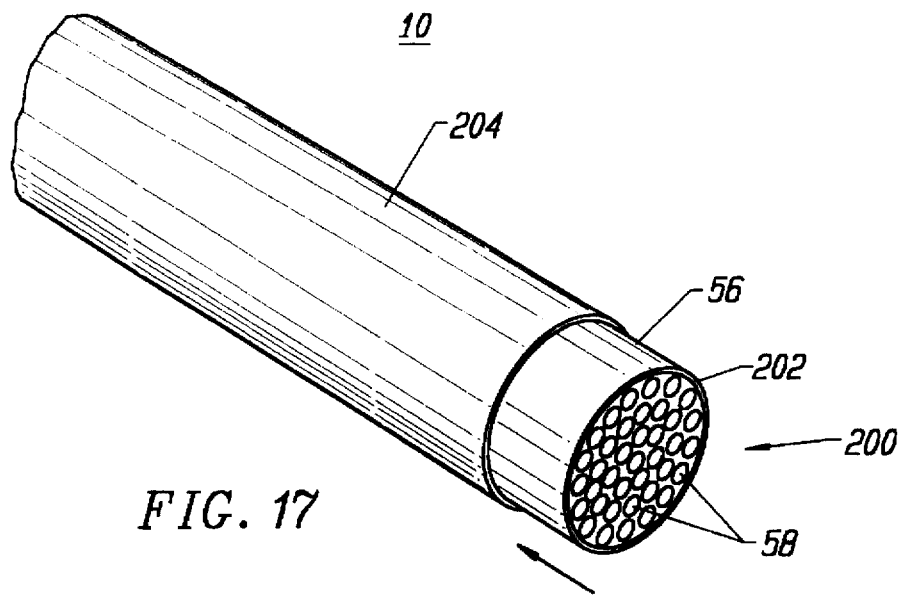
FIGS. 17 and 18 illustrate an electrosurgical probe having an electrode surface which can be transformed from a flat, circular array (FIG. 17) to an elongate, linear array (FIG. 18) suitable for use in surgical cutting.
Figure 18:
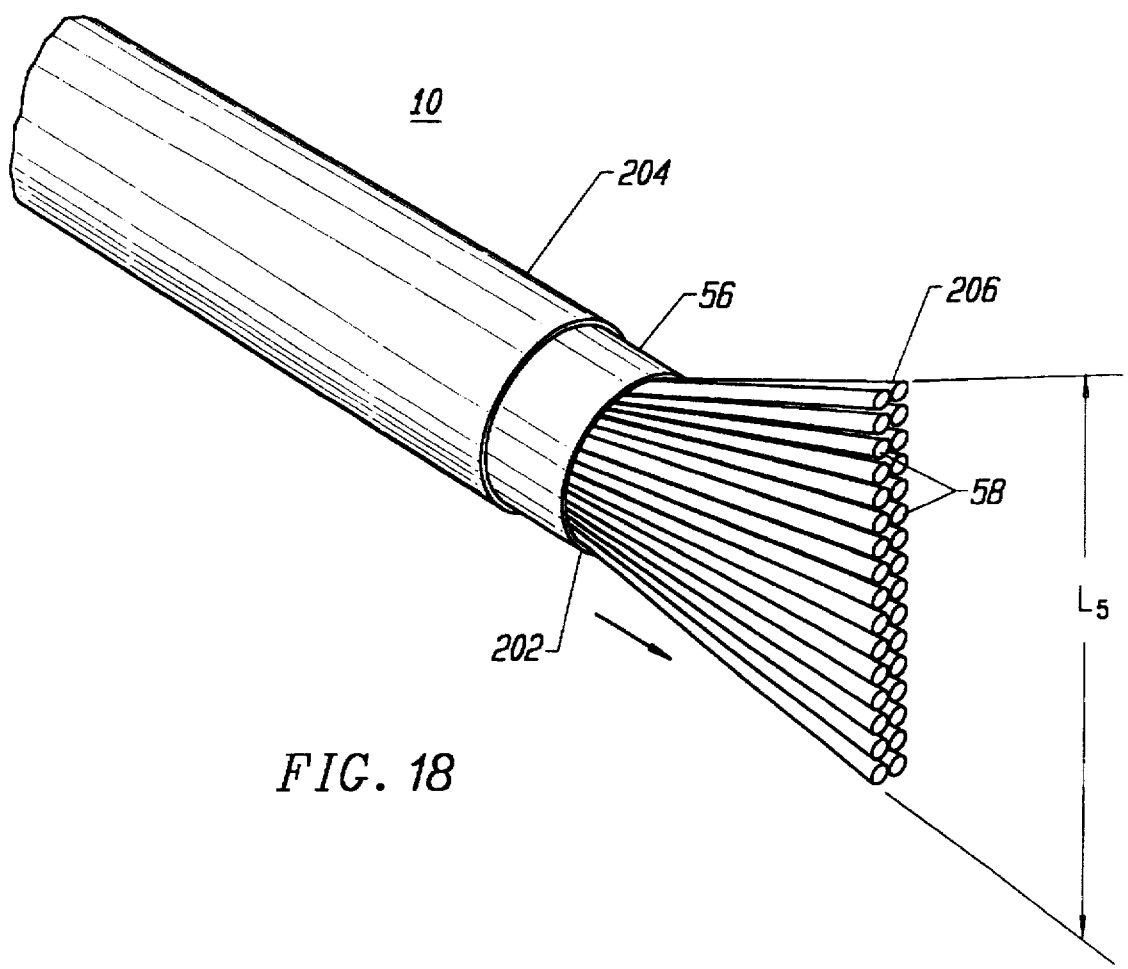

Another configuration for tip 200 of probe 10 is shown in FIGS. 17 and 18 and features a variable tip configuration which can be adjusted during the course of use of said probe 10. By way of example, tip 200 of probe 10 can be a cylindrical array of electrodes 58 which conforms to the cylindrical geometry of a rigid support member or cannula 202. The distal end of said cannula 202 may also serve as the common electrode 56 which is insulated in regions proximal to the tip region by an electrically insulating member 204. Referring now to FIG. 18, by extending the flexible array of electrodes 58 beyond the orifice of the cannula 202, an alternative electrode configuration can be obtained. By way of example, by placing a flat yet flexible member 206 between electrodes 58 as shown in FIG. 18, the electrode array can assume a flat "blade" shape configuration made up of a multiplicity of individual electrodes 58, each electrically insulated from all other electrodes. Such a configuration change may be advantageous if, after the insertion of the probe through a circular introduction port, the user can change the shape of the electrode array to achieve a flat "blade" shaped array whose width $L_5$ may be substantially greater than the circular electrode array configuration shown in FIG. 17. The increased width $L_5$ of the electrode array in FIG. 18 will provide the means for faster cutting through the target tissue since cutting depends primarily on the major dimension of the electrode array, either the diameter of the array (as shown in FIG. 17) or the width, $L_5$ of the array (as shown in FIG. 18). If the array width in FIG. 18 is three times as greater as the array diameter in FIG. 17, then the rate of cutting of the target tissue can be increased by approximately a factor of three. An additional benefit is that the depth of necrosis in tissue on either side of the cut made with the flat electrode configuration will be less than with the larger array used in a circular configuration.

What is claimed is:

1. A method for applying electrical energy to a target site on a structure within or on a patient's body, the method comprising:
   providing a return electrode and an electrode terminal electrically coupled to a high frequency voltage source;
   positioning an electrosurgical probe adjacent to the body structure so that an electrode terminal is brought into at least partial contact or close proximity with the target site;
   directing an electrically conducting fluid along a fluid path past a return electrode and to the target site and the electrode terminal to generate a current flow path between the electrode terminal and the return electrode; and
   applying high frequency voltage between the electrode terminal and the return electrode such that an electrical current flows from the electrode terminal, through the region of the target site, and to the return electrode through the current flow path.

2. The method of claim 1 wherein the probe is introduced into a substantially dry body cavity so that the target site is substantially electrically isolated from the return electrode prior to the directing step.

3. The method of claim 2 further including pressurizing the body cavity with a gas.

4. The method of claim 1 wherein the directing step includes supplying the electrically conducting fluid to a proximal end of an axial lumen defined by the return electrode within the probe and directing the fluid through a distal end of the axial lumen to the electrode terminal.

5. The method of claim 1 further including positioning a distal end of a fluid supply shaft adjacent the electrode terminal, the directing step including directing the electrically conducting fluid through an inner lumen in the fluid supply shaft that is electrically connected to the return electrode and discharging the fluid through an open distal end of the supply shaft towards the electrode terminal.

6. The method of claim 1 further comprising:
   applying high frequency voltage between the electrode terminal at or near the distal end of the probe and one or more return electrodes on or in the patient body; and
   controlling current flow through the electrode terminal to inhibit power dissipation into the electrically conducting fluid surrounding the target site.

7. The method of claim 6 wherein the tissue and electrical conducting fluid between the electrode terminal and the return electrode have an inherent capacitance, the method further comprising delivering high frequency current across a current limiting element in series with the electrode terminal.

8. The method of claim 7 further comprising selecting the current limiting element such that the inherent capacitance of the tissue and electrically conducting fluid between the electrode terminal and the return electrode combined with the associated current limiting element together form a series resonant output circuit.

9. The method of claim 8 further comprising changing the resonant frequency of a series resonant circuit with changes in the inherent capacitance between the electrode terminal and the return electrode.

10. The method of claim 7 further comprising passively limiting or interrupting of current flow to the electrode terminal with current limiting elements selected from the group consisting essentially of resistors, capacitors, inductors and combinations thereof.

11. The method of claim 6 further comprising actively limiting current to the electrode terminal based on the electrical impedance between the electrode terminal and the return electrode.

12. The method of claim 11 further comprising measuring current flow for a given applied voltage.

13. The method of claim 11 further comprising interrupting or limiting current between the electrode terminal and the return electrode when an impedance sensor indicates an electrical impedance less than a threshold level.

14. The method of claim 1 wherein the electrode terminal is surrounded and supported by an insulating matrix at or near the distal tip of the probe to electrically isolate the proximal portion of the electrode terminal from the electrically conducting fluid, the insulating matrix comprising an inorganic material.

15. The method of claim 14 wherein the inorganic material is selected from the group consisting essentially of ceramic, glass and glass/ceramic compositions.

16. A method as in claim 1, further including maintaining a space between the distal end of the electrode terminal and the structure during the applying step.

17. The method of claim 16 wherein the maintaining step comprises moving the electrode terminal transversely across the structure within or on the patient's body.

18. The method of claim 1 further comprising positioning a distal end of a fluid supply shaft adjacent the electrode terminal, the method further comprising directing the electrically conducting fluid through an inner lumen in the fluid supply shaft that is electrically connected to the high frequency voltage source and serves as the return electrode and discharging the electrically conducting fluid through an open distal end of the fluid supply shaft towards the electrode terminal.

19. The method of claim 1 wherein the electrode terminal is on a lateral surface of the electrosurgical probe.

20. The method of claim 1 wherein the return electrode is disposed proximally of the electrode terminal on the electrosurgical probe.

21. The method of claim 1 wherein the voltage applied between the electrode terminal and the return electrode is in the range from 10 volts (RMS) to 1000 volts (RMS).

22. The method of claim 1 wherein the height of the most distal portion of the electrode terminal relative to the most proximal portion of the electrode terminal exposed to the electrically conducting fluid is in the range from 0 to 2 mm.

23. The method of claim 1 wherein the distance between the most distal portion of the return electrode and the most proximal portion of the electrode terminal is in the range from 0.5 to 10 mm.

24. The method of claim 1 wherein the distal surface of the electrode terminal has a shape selected from the group consisting essentially of flat, concave, convex, hemispherical, linear (in-line), pyramidal, conical and cylindrical.

25. The method of claim 1 further comprising delivering high frequency current across a current limiting element in series with the electrode terminal.

26. The method of claim 1 wherein the power to the electrode terminal is controlled based on the electrical impedance between the electrode terminal and the return electrode.

27. The method of claim 26 further compromising limiting power to the electrode terminal when the electrical impedance is less than a threshold value.

28. The method of claim 1 wherein the electrode terminal and the return electrode are configured to effect the electrical breakdown of tissue in the immediate vicinity of the electrode terminal when high frequency voltage is applied between the electrode terminal and the return electrode in the presence of an electrically conducting fluid.

29. The method of claim 1 wherein temperature at the target site is measured by a temperature sensor adjacent the electrode terminal which is electrically coupled to the high frequency voltage source such that power delivery to the electrode terminal is limited if the measured temperature exceeds a threshold value.

30. The method of claim 29 wherein the temperature sensor is integral with the electrode terminal.

31. The method of claim 1 wherein the distal surface of the electrode terminal is circular in shape with a diameter in the range from 1 mm to 10 mm.

32. The method of claim 1 wherein the shape of the distal surface of the electrode terminal has an effective length of 1 mm to 20 mm and an effective width of 0.5 mm to 7.0 mm.

33. The method of claim 1 wherein the electrode terminal is configured for the cutting of tissue.

34. The method of claim 1 further comprising positioning a concave-shaped portion of the electrosurgical probe adjacent to the body structure so that the electrode terminal positioned within the concave shaped portion of the probe is brought into at least partial contact or close proximity with the target site.

35. The method of claim 1 further comprising positioning a lateral surface of the probe adjacent to the body structure so that the electrode terminal is brought into at least partial contact or close proximity with the tissue surfaces which are tangent to the electrosurgical probe.

36. The method of claim 1 wherein the electrode terminal is a flexible electrode terminal disposed at the distal tip of the probe, the flexible electrode terminal being extendable relative to the distal tip of the probe.

37. The method of claim 36 further comprising moving the electrode terminal relative to the distal tip of the probe to vary the shape of the electrode terminal.

38. The method of claim 1 wherein the return electrode is an inner tubular member defining an axial lumen electrically connected to the inner tubular member, the directing step including directing electrically conducting fluid through the inner lumen to the distal end of the probe over the electrode terminal.

39. The method of claim 1 wherein the return electrode is an outer tubular member defining an axial passage between the outer surface of the electrosurgical probe and the inner surface of said outer tubular member, the directing step including directing the electrically conducting fluid through the inner lumen to the distal end of the probe over the electrode terminal.

40. A method for applying electrical energy to a target site on a structure within or on a patient's body, the method comprising:

providing a return electrode and an array of two or more electrically isolated electrode terminals electrically coupled to a high frequency voltage source;

positioning an electrosurgical probe adjacent to the body structure so that one or more of the electrode terminals are brought into at least partial contact or close proximity with the target site;

directing an electrically conducting fluid along a fluid path past a return electrode and to the target site and the electrode terminals to generate a current flow path between electrode terminals and the return electrode; and applying high frequency voltage between the electrode terminals and the return electrode such that an electrical current flows from the electrode terminals, through the region of the target site, and to the return electrode through the current flow path.

41. The method of claim 40 wherein the return electrode is an inner tubular member defining an axial lumen electrically connected to the inner tubular member, the directing step including directing electrically conducting fluid through the inner lumen to the distal end of the shaft over the electrode terminals.

42. The method of claim 40 wherein the return electrode is an outer tubular member defining an axial passage between the outer surface of the electrosurgical probe and the inner surface of the outer tubular member, the directing step including directing the electrically conducting fluid through the inner lumen to the distal end of the probe over the electrode terminals.

43. A method as in claims 1 and 40, further including moving the electrode array transversely across a body structure within or on a patient's body.

44. The method of claim 40 further comprising applying high frequency voltage between the array of electrode terminals at or near the distal end of the probe and one or more return electrodes on or in the patient's body; and independently controlling current flow through the electrode terminals to inhibit power dissipation into the medium surrounding the target site.

45. The method of claim 44 wherein the tissue and the electrically conducting fluid between the electrode terminals and the return electrode have an inherent capacitance, the method further comprising delivering high frequency current across at least one current limiting element in series with one of the electrode terminals.

46. The method of claim 45 further comprising selecting the current limiting elements such that the inherent capacitance of the tissue and electrically conducting fluid between each electrode terminal and the return electrode combined with the associated current limiting element together form a series resonant output circuit.

47. The method of claim 46 further comprising changing the resonant frequency of a series resonant circuit with changes in the inherent capacitance of the tissue and the electrically conducting fluid between the electrode terminals and the return electrode.

48. The method of claim 44 further comprising actively limiting current to one or more of the electrode terminals based on the electrical impedance between the electrode terminal and the return electrode.

49. The method of claim 48 further comprising measuring current flow to each electrode terminal for a given applied voltage.

50. The method of claim 48 further comprising interrupting or limiting current between any individual electrode terminal in the electrode array and the return electrode when the impedance sensor indicates an electrical impedance is less than a threshold level.

51. The method of claim 44 further comprising passively limiting or interrupting current flow to each of the independent electrode terminals based on the electrical impedance between the electrode terminals and the return electrode.

52. The method of claim 44 further comprising passively limiting or interrupting of current flow to each of the electrode terminals with current limiting elements selected from the group consisting essentially of resistors, capacitors, inductors and combinations thereof.

53. The method of claim 40 wherein the electrode terminals are surrounded and supported by an insulating matrix at or near the distal tip of the probe to electrically isolate each electrode terminal from one another and to electrically isolate the proximal portions of the electrode terminals from the electrically conducting fluid, the insulating matrix comprising an inorganic material.

54. The method of claim 53 wherein the inorganic material is selected from the group consisting essentially of ceramic, glass, and glass/ceramic compositions.

55. The method as in claim 40, further including maintaining a space between the distal ends of electrode terminals and the structure within or on a patient's body during the applying step.

56. The method of claim 55 wherein the maintaining step comprises moving the electrode terminal transversely across the structure within or on a patient's body.

57. The method of claim 40 further comprising positioning a distal end of a fluid supply shaft adjacent the electrode terminals, the method further comprising directing the electrically conducting fluid through an inner lumen in the fluid supply shaft that is electrically connected to the high frequency voltage source and serves as the return electrode and discharging the electrically conducting fluid through an open distal end of the fluid supply shaft toward the electrode terminals.

58. The method of claim 40 wherein the array of electrode terminals is on a lateral surface of the probe.

59. The method of claim 40 wherein the return electrode is disposed proximally of the electrode terminals on the electrosurgical probe.

60. The method of claim 40 wherein the voltage applied between the electrode terminals and the return electrode is in the range from 10 volts (RMS) to 1000 volts (RMS).

61. The method of claim 40 wherein the height of the most distal portion of any of the electrode terminals relative to the most proximal portion of said electrode terminals exposed to the electrically conducting fluid is in the range from 0 to 2 mm.

62. The method of claim 40 wherein the distance between the most distal portion of the return electrode and the most proximal portion of any of the electrode terminals is in the range from 0.5 to 10 mm.

63. The method of claim 40 wherein the distal surface of the array of electrode terminals may be flat, concave, convex, hemispherical, linear (in-line), pyramidal, conical and cylindrical.

64. The method of claim 40 further including positioning a distal end of a fluid supply shaft adjacent the electrode terminal, the directing step including directing the electrically conducting fluid through an inner lumen in the fluid supply shaft that is electrically connected to the return electrode and discharging the fluid through an open distal end of the supply shaft towards the electrode terminals.

65. The method of claim 64 further including controlling flow of the electrically conducting fluid through the fluid path with a control valve on the probe.

66. The method of claim 40 further comprising delivering high frequency current across at least one current limiting element in series with one of the electrode terminals.

67. The method of claim 40 wherein the power to the electrode terminals is independently controlled based on the electrical impedance between each of the electrode terminals and the return electrode.

68. The method of claim 67 further comprising independently limiting power to the electrode terminals when the electrical impedance between any electrode terminal and the return electrode is less than a threshold value.

69. The method of claim 40 wherein the electrode terminal and the return electrode are configured to effect the electrical breakdown of tissue in the immediate vicinity of ore or more of the electrode terminals when high frequency voltage is applied between the electrode terminals and the return electrode in the presence of an electrically conducting fluid.

70. The method of claim 40 wherein temperature at the target site is measured by a temperature sensor adjacent the electrode terminals which is electrically coupled to the high frequency voltage source such that power delivery to one or more of the electrode terminals is limited if the measured temperature exceeds a threshold value.

71. The method of claim 70 wherein at least one of the temperature sensors is integral with at least one of the electrodes within the electrode array.

72. The method of claim 40 wherein the distal surface of the array of electrode terminals is circular in shape with a diameter in the range from 1 mm to 10 mm.

73. The method of claim 40 wherein the shape of the distal surface of the array of electrode terminals has an effective length of 1 mm to 20 mm and an effective width of 0.5 mm to 7.0 mm.

74. The method of claim 40 wherein the array of electrode terminals are configured for the cutting of tissue.

75. The method of claim 40 further comprising positioning a concave-shaped portion of the electrosurgical probe adjacent to the body structure so that one or more of the electrode terminals positioned within the concave shaped portion of the probe are brought into at least partial contact or close proximity with the target site.

76. The method of claim 40 further comprising positioning a lateral surface of the probe adjacent to the body structure so that one or more of the electrode terminals are brought into at least partial contact or close proximity with the tissue surfaces which are tangent to the electrosurgical probe.

77. The method of claim 40 wherein the array of electrode terminals is a flexible array of electrode terminals disposed at the distal end of the probe, the flexible array of electrode terminals being extendable relative to the distal tip of the probe.

78. The method of claim 77 further comprising moving the flexible array of electrode terminals relative to the distal tip of the probe to vary the shape of the array of electrode terminals.

79. The method of claim 40 wherein the directing step includes supplying the electrically conducting fluid to a proximal end of an axial lumen defined by the return electrode within the probe and directing the fluid through a distal end of the axial lumen to the array of electrode terminals.

80. The method of claims 1 and 40 wherein the electrically conducting fluid is directed to the target site before the positioning step.

81. The method of claims 1 and 40 wherein the electrically conducting fluid is directed to the target site during the positioning step.

82. The method of claims 1 and 40 wherein the electrically conducting fluid is directed to the target site after the positioning step.

83. The method of claims 1 and 40 wherein the probe is introduced into a body cavity and the electrically conducting fluid is directed into a body cavity to substantially fill the body cavity with the fluid, and wherein the return electrode is positioned within the body cavity in contact with the fluid therein to generate a current flow path between the target site and the return electrode.

84. The method of claim 83 wherein the electrically conducting fluid is directed through a cannula into the body cavity, each electrode terminal and the return electrode being submerged in the fluid within the body cavity.

85. The method of claims 1 and 40 further comprising applying sufficient electrical energy between each electrode terminal and the return electrode to effect ablation of tissue adjacent each electrode terminal such that a portion of said tissue is volumetrically removed.

86. The method of claims 1 and 40 wherein the frequency of the voltage applied between the active and return electrodes is in the range of 20 kHz and 20 MHz.

87. The method of claims 1 and 40 wherein the electrically conducting fluid is selected from the group consisting essentially of blood and electrolytic irrigants.

88. The method of claim 87 wherein the electrically conducting fluid comprises isotonic saline.

89. The method of claims 1 and 40 further comprising generating a high electric field intensity at a distal portion of the electrode terminal or terminals.

90. The method of claim 89 wherein the electric field intensity is sufficient to cause molecular disintegration of a structure at the target site within or on a patient's body.

91. The method of claims 1 and 40 wherein the body cavity is selected from the group consisting essentially of the abdominal cavity and thoracic cavity.

92. The method of claims 1 and 40 wherein the target site is the knee, shoulder, hip, hand, foot, elbow and spine.

93. The method of claims 1 and 40 wherein the target site is in the patient's mouth.

94. The method of claims 1 and 40 wherein the target site is in the ear, nose or throat.

95. The method of claims 1 and 40 wherein the target site is accessible via a natural body orifice.

96. The method of claims 1 and 40 wherein the target site is accessible on the surface of the patient's body.

97. The method of claim 96 wherein the target site includes the epidermis or dermis of the patient's body.

98. The method of claims 1 and 40 wherein the electrode terminal or electrode terminals are disposed at the distal tip of the electrosurgical probe.

99. The method of claims 1 and 40 wherein the target site is a tumor.

100. The method of claims 1 and 40 further comprising a flexible shaft include an actuator at the proximal end of the shaft, the method further comprising selectably deflecting the distal end of the shaft with the actuator.

101. A method for applying electrical energy to a target site on a structure within or on a patient's body, the method comprising:

providing a return electrode and an electrode terminal electrically coupled to a high frequency voltage source;

positioning an electrosurgical probe adjacent to the body structure so that an electrode terminal is brought into at least partial contact or close proximity with the target site;

directing an electrically conducting fluid to the target site and the electrode terminal to surround the electrode terminal with electrically conducting fluid and to locate electrically conducting fluid between the electrode terminal and the target site; and applying high frequency voltage between the electrode terminal and the return electrode such that an electrical current flows from the electrode terminal, through the region of the target site, and to the return electrode.

102. The method of claim 101 wherein the return electrode is located on the surface of the patient's body.

103. A method for applying electrical energy to a target site on a structure within or on a patient's body, the method comprising:

providing a return electrode and an array of electrode terminals electrically coupled to a high frequency voltage source;

positioning an electrosurgical probe adjacent to the body structure so that one or more of the electrode terminals are brought into at least partial contact or close proximity with the target site;

directing an electrically conducting fluid to the target site and electrode terminals to surround the electrode terminals with electrically conducting fluid and to locate electrically conducting fluid between the electrode terminals and the target site; and applying high frequency voltage between the electrode terminals and the return electrode such that an electrical current flows from the electrode terminals, through the region of the target site, and to the return electrode.

104. The method of claim 103 wherein the return electrode is located on the surface of the patient's body.

* * * * *